(12) United States Patent
Morishita et al.

(10) Patent No.: US 8,008,512 B2
(45) Date of Patent: Aug. 30, 2011

(54) PYRIDAZINE COMPOUND AND USE THEREOF

(75) Inventors: Hiroshi Morishita, Oita (JP); Akio Manabe, Sanda (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 283 days.

(21) Appl. No.: 12/458,433

(22) Filed: Jul. 13, 2009

(65) Prior Publication Data

US 2009/0281337 A1 Nov. 12, 2009

Related U.S. Application Data

(62) Division of application No. 11/628,264, filed as application No. PCT/JP2005/010204 on May 27, 2005, now Pat. No. 7,569,518.

(30) Foreign Application Priority Data

Jun. 9, 2004 (JP) .................... 2004-170823

(51) Int. Cl.
C07D 307/33 (2006.01)

(52) U.S. Cl. ..................................... 549/313

(58) Field of Classification Search .................. 549/313
See application file for complete search history.

(56) References Cited

U.S. PATENT DOCUMENTS 3,790,571 A  2/1974  Diskus et al.

FOREIGN PATENT DOCUMENTS

| JP | 55-111472 A | 8/1980 |
| JP | 56-113767 A | 9/1981 |
| WO | WO 96/36623 A1 | 11/1996 |
| WO | WO 99/10331 A1 | 3/1999 |

OTHER PUBLICATIONS

Pattabiraman, V. R. et al., "Synthesis of 3,4-Diarylsubstituted Maleic Anhydride/Maleimide via Unusual Oxidative Cyclization of Phenacyl Ester/Amide", Synlett, 2002, No. 4, pp. 947-951.

Lai, Y. H. et al., "Synthesis and Diatropicity of trans-N-Cyclohexyl-2', 5', 10b,10-tetramethylpyrrolo [3,4-e]—10b-dihydropyrene. The First Example of an Iso [17] annulenopyrrole", Journal of Organic Chemistry, 1997, vol. 62, No. 17, pp. 6060-6063.

Black, W. C. et al., "3,4-Diaryl-5-hydroxyfuranones: Highly Selective Inhibitors of Cyclooxygenase-2 with Aqueous Solubility", Bioorganic & Medical Chemistry Letter 13, 2003, pp. 1195-1198.

Krapf, H. et al., "Thermische Umwandlung der labilen 1 : 1-Addukte aus Diphenylcyclopropenon bzw. Diphenylcyclopropenthion und Ketenacetalen", Chemischeberichte, 1976, vol. 109. No. 2, pp. 576-596.

Chambers, R. et al., "Polyfluoroheterocyclic Compounds. Part XXIV. Thermal Elimination of Molecular Nitrogen from Polyfluoro- and Polychloro-pyridazines", J. Chem. Soc. (1), 1974, pp. 125-129.

Klyuev N. A., et al., "Chromatographic-mass spectrometric study of azines of alkyl benzyl ketones and products of thief thermal transformation", Zhurnal Organicheskoi Khimii, 1979, 15 (11), pp. 2274-2280.

Berry, R. W. H. et al., "4,5-Diphenylpyridazine: Preparation and Ultraviolet Spectrum", J. Chem. Soc. (C), 1970, p. 1316.

Primary Examiner — Bernard Dentz
(74) Attorney, Agent, or Firm — Foley & Lardner LLP

(57) ABSTRACT

A pyridazine compound represented by formula (1):

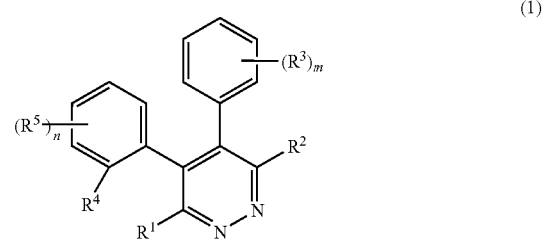

has an excellent plant disease controlling effect.

1 Claim, No Drawings

PYRIDAZINE COMPOUND AND USE THEREOF

This application is a divisional application of U.S. Ser. No. 11/628,264, filed Mar. 2, 2007, which is the National Stage application of International Application No. PCT/JP2005/010204, filed May 27, 2005. International Application No. PCT/JP2005/010204 claims the benefit of Japan Application No. 2004-170823, filed on Jun. 9, 2004. All of which are hereby incorporated by reference in their entirety.

BACKGROUND OF THE INVENTION

1. Technical Field

The present invention relates to a pyridazine compound, use thereof and its production intermediate.

2. Background Art

Conventionally, agricultural fungicides have been developed, and a lot of compounds having a fungicidal activity have been found. However, a plant disease controlling effect of these compound's is not necessarily sufficient, and novel compounds having a plant disease controlling effect are searched.

DISCLOSURE OF THE INVENTION

The present inventors have intensively studied to find a compound having an excellent plant disease controlling effect, and resultantly found that a pyridazine compound represented by the following formula (1) has an excellent plant disease controlling activity, completing the present invention.

That is, the present invention is as described in the following items 1 to 7.

1. A pyridazine compound represented by formula (1) (referred as the compound of the present invention, hereinafter):

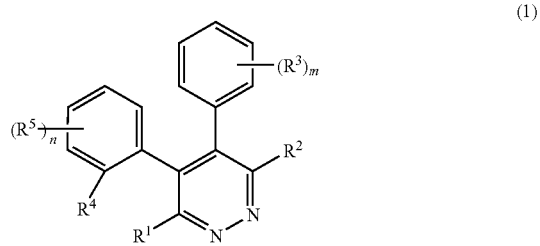

wherein,
$R^1$ represents a chlorine atom, a bromine atom or a C1-C4 alkoxy group;
$R^2$ represents a C1-C4 alkyl group;
$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;
m represents an integer of 0 to 5; provided that, when m represents an integer of 2 or more, each of $R^3$s is same or different;
$R^4$ represents a halogen atom, a nitro group, a cyano group, a C1-C4 alkyl group optionally substituted by at least one halogen atom or a C1-C4 alkoxy group optionally substituted by at least one halogen atom;
$R^5$ represents a halogen atom, a nitro group, a cyano group, a C1-C4 alkyl group optionally substituted by at least one halogen atom or a C1-C4 alkoxy group optionally substituted by at least one halogen atom;
n represents an integer of 0 to 4; provided that, when n represents an integer of 2 or more, each of $R^5$s is same or different.

2. A fungicidal composition comprising the compound of the present invention as an active ingredient.

3. A method for controlling plant diseases comprising a step applying an effective amount of the compound of the present invention to plants or soils growing the plants.

4. Use of the compound of the present invention as an active ingredient of a fungicidal composition.

5. A compound represented by formula (2):

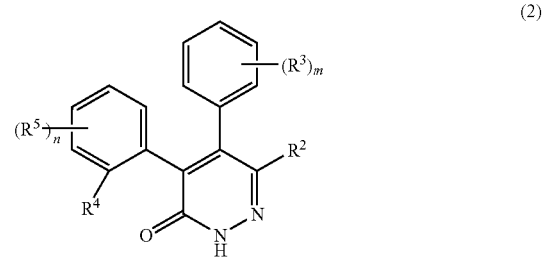

wherein,
$R^2$ represents a C1-C4 alkyl group;
$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;
m represents an integer of 0 to 5; provided that, when m represents an integer of 2 or more, each of $R^3$s is same or different;
$R^4$ represents a halogen atom, a nitro group, a cyano group, a C1-C4 alkyl group optionally substituted by at least one halogen atom or a C1-C4 alkoxy group optionally substituted by at least one halogen atom;
$R^5$ represents a halogen atom, a nitro group, a cyano group, a C1-C4 alkyl group optionally substituted by at least one halogen atom or a C1-C4 alkoxy group optionally substituted by at least one halogen atom;
n represents an integer of 0 to 4; provided that, when n represents an integer of 2 or more, each of $R^5$s is same or different.

6. A compound represented by formula (1-3):

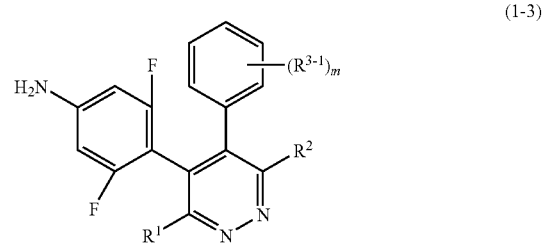

wherein,
$R^1$ represents a chlorine atom, a bromine atom or a C1-C4 alkoxy group;
$R^2$ represents a C1-C4 alkyl group;

$R^{3-1}$ represents a halogen atom, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;

m represents an integer of 0 to 5; provided that, when m represents an integer of 2 or more, each of $R^{3-1}$s is same or different.

7. A compound represented by formula (3):

$$(3)$$

wherein,
$R^2$ represents a C1-C4 alkyl group;
$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;
m represents an integer of 0 to 5; provided that, when m represents an integer of 2 or more, each of $R^3$s is same or different;
$R^4$ represents a halogen atom, a nitro group, a cyano group, a C1-C4 alkyl group optionally substituted by at least one halogen atom or a C1-C4 alkoxy group optionally substituted by at least one halogen atom;
$R^5$ represents a halogen atom, a nitro group, a cyano group, a C1-C4 alkyl group optionally substituted by at least one halogen atom or a C1-C4 alkoxy group optionally substituted by at least one halogen atom;
n represents an integer of 0 to 4; provided that, when n represents an integer of 2 or more, each of $R^5$s is same or different.

Next, substituents on the compounds of the present invention and the like will be described.

As the substituent on the compound of the present invention represented by the formula (1), the compound represented by the formula (2), the compound represented by the formula (1-3) and the compound represented by the formula (3) of the present invention, groups shown below are exemplified.

The C1-C4 alkoxy group represented by $R^1$ includes, for example, a methoxy group and an ethoxy group.

The C1-C4 alkyl group represented by $R^2$ includes, for example, a methyl group and an ethyl group.

The C1-C4 alkyl group optionally substituted by at least one halogen atom represented by $R^3$ or $R^{3-1}$ includes, for example, a methyl group, an ethyl group, an isopropyl group, a tert-butyl group, a trifluoromethyl group, a difluoromethyl group and a fluoromethyl group;

the C1-C4 alkoxy group optionally substituted by at least one halogen atom includes, for example, a methoxy group, an ethoxy group, an isopropoxy group, a trifluoromethoxy group, a difluoromethoxy group, a fluoromethoxy group, a chlorodifluoromethoxy group, a bromodifluoromethoxy group, a 1,1,2,2-tetrafluoroethoxy group and a 2,2,2-trifluoroethoxy group;

the C1-C4 alkylthio group optionally substituted by at least one halogen atom includes, for example, a methylthio group, an ethylthio group, a trifluoromethylthio group and a 1,1,2,2-tetrafluoroethylthio group, and the halogen atom represented by $R^3$, $R^{3-1}$, $R^4$ and $R^5$ includes a fluorine atom, a chlorine atom, a bromine atom and an iodine atom.

The C1-C4 alkyl group optionally substituted by at least one halogen atom represented by $R^4$ and $R^5$ includes, for example, a methyl group, an ethyl group, a trifluoromethyl group, a difluoromethyl group and a fluoromethyl group, and the C1-C4 alkoxy group optionally substituted by at least one halogen atom includes, for example, a methoxy group, an ethoxy group, a trifluoromethoxy group, a difluoromethoxy group and a fluoromethoxy group.

The phenyl group substituted by $R^4$ and $(R^5)_n$ includes, for example, groups in which n is 0, that is, a 2-chlorophenyl group, a 2-fluorophenyl group, a 2-nitrophenyl group, a 2-cyanophenyl group, a 2-methylphenyl group, a 2-(trifluoromethyl)phenyl group, a 2-methoxyphenyl group, a 2-(difluoromethoxy)phenyl group, a 2-(trifluoromethoxy)phenyl group; groups in which n is 1, that is, a 2,3-difluorophenyl group, a 2,3-dichlorophenyl group, a 2,4-difluorophenyl group, a 2-chloro-4-fluorophenyl group, a 4-chloro-2-fluorophenyl group, a 2,4-dichlorophenyl group, a 2,5-difluorophenyl group, a 2,6-difluorophenyl group, a 2-chloro-6-fluorophenyl group, a 2,6-dichlorophenyl group, a 2-fluoro-6-methylphenyl group, a 2-fluoro-6-nitrophenyl group, a 2-cyano-6-fluorophenyl group, a 2-fluoro-6-(trifluoromethyl)phenyl group, a 2-(difluoromethoxy)-6-fluorophenyl group, a 2-fluoro-6-(trifluoromethoxy)phenyl group, a 2-fluoro-6-methoxyphenyl group; groups in which n is 2, that is, a 2,3,4-trifluorophenyl group, a 2,3,5-trifluorophenyl group, 2,4,5-trifluorophenyl group, a 2,3,6-trifluorophenyl group, a 2,4,6-trifluorophenyl group, a 2-chloro-4,6-difluorophenyl group, a 4-chloro-2,6-difluorophenyl group, a 2,6-difluoro-4-ethoxyphenyl group, a 2,6-difluoro-4-methoxyphenyl group, a 2,4-dichloro-6-fluorophenyl group, a 2,6-dichloro-4-fluorophenyl group, a 2,4,6-trichlorophenyl group, a 2,6-difluoro-4-cyanophenyl group, a 2,6-difluoro-4-nitrophenyl group, a 2,6-difluoro-4-(trifluoromethyl)phenyl group, a 2,3-difluoro-6-(trifluoromethyl)phenyl group, a 2,6-difluoro-3-chlorophenyl group; groups in which n is 3, that is, a 2,3,4,5-tetrafluorophenyl group, a 2,3,4,6-tetrafluorophenyl group, a 2,3,5,6-tetrafluorophenyl group; groups in which n is 4, that is, a 2,3,4,5,6-pentafluorophenyl group, a 4-methoxy-2,3,5,6-tetrafluorophenyl group, a 4-ethoxy-2,3,5,6-tetrafluorophenyl group, a 4-cyano-2,3,5,6-tetrafluorophenyl group, a 4-nitro-2,3,5,6-tetrafluorophenyl group and a 4-chloro-2,3,5,6-tetrafluorophenyl group.

The phenyl group substituted by $(R^3)$ m includes, for example, a phenyl group; groups in which m is 1, that is, a 4-methylphenyl group, a 3-methylphenyl group, a 2-methylphenyl group, a 4-ethylphenyl group, a 4-isopropylphenyl group, a 4-tert-butylphenyl group, a 4-(trifluoromethyl)phenyl group, a 3-(trifluoromethyl)phenyl group, a 4-chlorophenyl group, a 3-chlorophenyl group, a 2-chlorophenyl group, a 4-fluorophenyl group, a 3-fluorophenyl group, a 2-fluorophenyl group, a 4-methoxyphenyl group, a 3-methoxyphenyl group, a 4-ethoxyphenyl group, a 4-(trifluoromethoxy)phenyl group, a 4-nitrophenyl group, a 4-cyanophenyl group, a 4-(methylthio)phenyl group, a 4-(trifluoromethythio)phenyl group; groups in which m is 2, that is, a 2,4-dimethylphenyl group, a 2,5-dimethylphenyl group, a 3,4-dimethylphenyl group, a 2,4-dichlorophenyl group, a 2,5-dichlorophenyl group, a 3,4-dichlorophenyl group, a 2,3-difluorophenyl group, a 2,4-difluorophenyl group, a 2,5-difluorophenyl group, a 3,4-difluorophenyl group, a 3,5-difluorophenyl group, a 4-chloro-2-fluorophenyl group, a 2,4-dimethoxyphenyl group and a 3,4-dimethoxyphenyl group.

Embodiments of the compound of the present invention include, for example, the following compounds in the compounds of the present invention.

Pyridazine compounds of the formula (1) in which $R^1$ is a chlorine atom or a bromine atom;

pyridazine compounds of the formula (1) in which $R^1$ is a C1-C4 alkoxy group;

pyridazine compounds of the formula (1) in which $R^1$ is a chlorine atom and $R^2$ is a methyl group;

pyridazine compounds of the formula (1) in which $R^1$ is a methoxy group and $R^2$ is a methyl group;

pyridazine compounds of the formula (1) in which $R^3$ is a C1-C4 alkyl group optionally substituted by at least one halogen atom, a C1-C4 alkoxy group optionally substituted by at least one halogen atom, or a halogen atom;

pyridazine compounds of the formula (1) in which $R^3$ is a C1-C4 alkyl group or a halogen atom;

pyridazine compounds of the formula (1) in which $R^3$ is a methyl group, a trifluoromethyl group, a chlorine atom, a fluorine atom or a methoxy group;

pyridazine compounds of the formula (1) in which $R^3$ is a methyl group, a chlorine atom or a fluorine atom;

pyridazine compounds of the formula (1) in which m is 1 or 2;

pyridazine compounds of the formula (1) in which m is 1;

pyridazine compounds of the formula (1) in which m is 2;

pyridazine compounds of the formula (1) in which m is 1 and $R^3$ is a substituent at 4-position of benzene ring;

pyridazine compounds of the formula (1) in which m is 1, $R^3$ is a halogen atom, a C1-C4 alkyl group optionally substituted by at least one halogen atom or a C1-C4 alkoxy group optionally substituted by at least one halogen atom, and $R^3$ is a substituent at 4-position of benzene ring;

pyridazine compounds of the formula (1) in which m is 1, $R^3$ is a halogen atom or a C1-C4 alkyl group optionally substituted by at least one halogen atom, and $R^3$ is a substituent at 4-position of benzene ring;

pyridazine compounds of the formula (1) in which m is 1, $R^3$ is a halogen atom or a C1-C4 alkyl group, and $R^3$ is a substituent at 4-position of benzene ring;

pyridazine compounds of the formula (1) in which m is 1, $R^3$ is a methyl group, a trifluoromethyl group, a chlorine atom, a fluorine atom or a methoxy group, and $R^3$ is a substituent at 4-position of benzene ring;

pyridazine compounds of the formula (1) in which m is 1, $R^3$ is a methyl group, a chlorine atom or a fluorine atom, and $R^3$ is a substituent at 4-position of benzene ring;

pyridazine compounds of the formula (1) in which $R^4$ is a halogen atom;

pyridazine compounds of the formula (1) in which $R^4$ is a fluorine atom;

pyridazine compounds of the formula (1) in which $R^4$ is a chlorine atom;

pyridazine compounds of the formula (1) in which $R^4$ is a fluorine atom or a chlorine atom;

pyridazine compounds of the formula (1) in which n is 0, 1 or 2;

pyridazine compounds of the formula (1) in which n is 0;

pyridazine compounds of the formula (1) in which n is 1;

pyridazine compounds of the formula (1) in which n is 2;

pyridazine compounds of the formula (1) in which n is 1 or 2 and $R^5$ is a halogen atom, pyridazine compounds of the formula (1) in which n is 1, $R^5$ is a halogen atom, and $R^5$ is a substituent at 4-position or 6-position of benzene ring;

pyridazine compounds of the formula (1) in which n is 2, $R^5$ is a halogen atom, and $R^5$ is a substituent at 4-position or 6-position of benzene ring;

pyridazine compounds of the formula (1) in which n is 1, $R^5$ is a fluorine atom, and $R^5$ is a substituent at 4-position or 6-position of benzene ring;

pyridazine compounds of the formula (1) in which n is 2, $R^5$ is a fluorine atom, and $R^5$ is a substituent at 4-position or 6-position of benzene ring;

pyridazine compounds of the formula (1) in which $R^4$ is a halogen atom, n is 1 or 2, and $R^5$ is a halogen atom;

pyridazine compounds of the formula (1) in which n is 1, $R^4$ is a halogen atom, $R^5$ is a halogen atom, and $R^5$ is a substituent at 4-position or 6-position of benzene ring;

pyridazine compounds of the formula (1) in which n is 2, $R^4$ is a halogen atom, $R^5$ is a halogen atom, and $R^5$ is a substituent at 4-position or 6-position of benzene ring;

pyridazine compounds of the formula (1) in which n is 1, $R^4$ is a fluorine atom, $R^5$ is a fluorine atom, and $R^5$ is a substituent at 4-position or 6-position of benzene ring;

pyridazine compounds of the formula (1) in which n is 2, $R^4$ is a fluorine atom, $R^5$ is a fluorine atom, and $R^5$ is a substituent at 4-position or 6-position of benzene ring;

pyridazine compounds of the formula (1) in which m is 1 or 2, and n is 0, 1 or 2;

pyridazine compounds of the formula (1) in which $R^1$ is a chlorine atom or a bromine atom, $R^2$ is a methyl group, and $R^4$ is a halogen atom; and pyridazine compounds of the formula (1) in which m is 1 or 2, n is 0, 1 or 2, $R^1$ is a chlorine atom or a bromine atom, $R^2$ is a methyl group, and $R^4$ is a halogen atom.

Embodiments of the compound represented by the formula (2), the compound represented by the formula (1-3) and the compound represented by the formula (3), which are intermediates of the compound of the present invention, include, for example, compounds described below.

Embodiments of the compound represented by the formula (2) include, for example, the following compounds.

Compounds of the formula (2) in which m is 1 or 2, and n is 0, 1 or 2;

compounds of the formula (2) in which $R^2$ is a methyl group, and $R^4$ is a halogen atom; and compounds of the formula (2) in which m is 1 or 2, n is 0, 1 or 2, $R^2$ is a methyl group, and $R^4$ is a halogen atom.

Embodiments of the compound represented by the formula (1-3) include, for example, the following compounds.

Compounds of the formula (1-3) in which m is 1 or 2;

compounds of the formula (1-3) in which $R^1$ is a chlorine atom or a bromine atom, $R^2$ is a methyl group, and $R^4$ is a halogen atom; and compounds of the formula (1-3) in which m is 1 or 2, $R^1$ is a chlorine atom or a bromine atom, $R^2$ is a methyl group, and $R^4$ is a halogen atom.

Embodiments of the compound represented by the formula (3) include, for example, the following compounds.

Compounds of the formula (3) in which m is 1 or 2, and n is 0, 1 or 2;

compounds of the formula (3) in which $R^2$ is a methyl group, and $R^4$ is a halogen atom; and compounds of the formula (3) in which m is 1 or 2, n is 0, 1 or 2, $R^2$ is a methyl group, and $R^4$ is a halogen atom.

Next, the method of producing the compound of the present invention will be described;

The compound of the present invention can be produced, for example, by the following (Production method 1), (Production method 2) and (Production method 3).

(Production Method 1)

The compound represented by the formula (1-1) in which $R^1$ is a chlorine atom or a bromine atom, among the compounds of the present invention, can be produced by reacting the compound represented by the formula (2) with a halogenating agent.

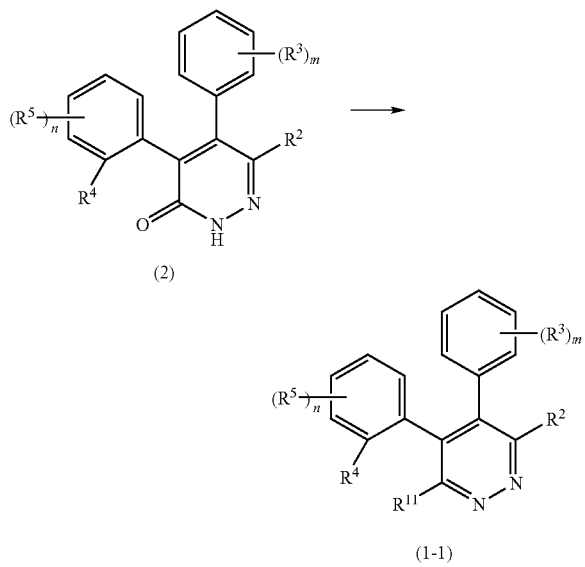

(wherein, $R^2$ is a C1-C4 alkyl group, $R^3$ is a halogen atom, a nitro group, a cyano group, a C1-C4 alkyl group optionally substituted by at least one halogen atom, a C1-C4 alkoxy group optionally substituted by at least one halogen atom, or a C1-C4 alkylthio group optionally substituted by at least one halogen atom, m is an integer of 0 to 5; provided that, when m is an integer of 2 or more, each of $R^3$s is same or different;

$R^4$ is a halogen atom, a nitro group, a cyano group, a C1-C4 alkyl group optionally substituted by at least one halogen atom or a C1-C4 alkoxy group optionally substituted by at least one halogen atom, $R^5$ is a halogen atom, a nitro group, a cyano group, a C1-C4 alkyl group optionally substituted by at least one halogen atom or a C1-C4 alkoxy group optionally substituted by at least one halogen atom, n is an integer of 0 to 4; provided that, when n is an integer of 2 or more, each of $R^5$s is same or different.

$R^{11}$ is a chlorine atom or a bromine atom.).

The reaction is carried out in the absence or presence of a solvent.

Examples of the solvent used in the reaction include hydrocarbons such as toluene, xylene and the like, halogenated hydrocarbons such as chlorobenzene, dichlorobenzene and the like, and mixtures thereof.

The halogenating agent used in the reaction includes, for example, chlorinating agents such as phosphorus oxychloride, phosphorus pentachloride, and brominating agents such as phosphorus oxybromide, phosphorus pentabromide, and the like.

The amount of the halogenating agent used in the reaction is usually a proportion of 1 to 20 mol per 1 mol of the compound represented by the formula (2).

The reaction temperature is usually in a range of 20 to 120° C., and the reaction time is usually in a range of 0.1 to 8 hours.

After completion of the reaction, for example, the reaction mixture is subjected to a post treatment operation such as the reaction mixture being concentrated, water being added to the residue and extracting with an organic solvent, and the resulting organic layer being dried, concentration and the like; thus, the compound represented by the formula (1-1) can be isolated. The compound represented by the formula (1-1) isolated can also be further purified by chromatography, recrystallization and the like.

(Production Method 2)

The compound represented by the formula (1-2) in which $R^1$ is a C1-C4 alkoxy group, among the compounds of the present invention, can be produced by reacting the compound represented by the formula (1-1) with an alcoholate compound represented by the formula:

$$NaR^{12}$$

(wherein, $R^{12}$ is a C1-C4 alkoxy group).

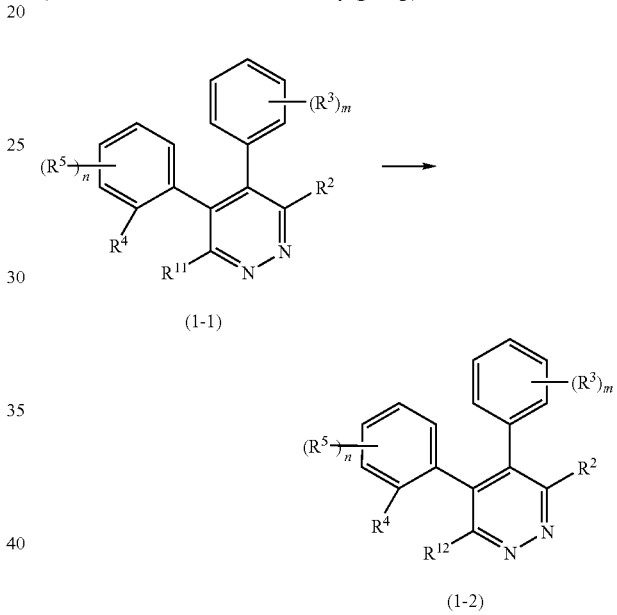

(wherein, $R^{11}$, $R^2$, $R^3$, m, $R^4$, $R^5$, n and $R^{12}$ are the same meanings as described above).

The reaction is carried out usually in a solvent.

Examples of the solvent used in the reaction include alcohols represented by the formula $R^{12}H$, ethers such as tetrahydrofuran, 1,2-dimethoxyethane and the like, and mixtures thereof.

The amount of the alcoholate compound used in the reaction is usually a proportion of 1 to 20 mol per 1 mol of the compound represented by the formula (1-1).

The reaction temperature is usually in a range of 0 to 120° C., and the reaction time is usually in a range of 1 to 72 hours.

After completion of the reaction, for example, the reaction mixture is subjected to a post treatment operation such as water being added to the reaction mixture and extracting with an organic solvent, and the resulting organic layer being dried, concentration and the like; thus, the compound represented by the formula (1-2) can be isolated. The compound represented by the formula (1-2) isolated can also be further purified by chromatography, re-crystallization and the like.

(Production Method 3)

The compound represented by the formula (1-4), among the compounds of the present invention, can be produced by reacting the compound represented by the formula (1-3) with alkyl nitrite and copper halide (II).

(Reference Production Method 1)

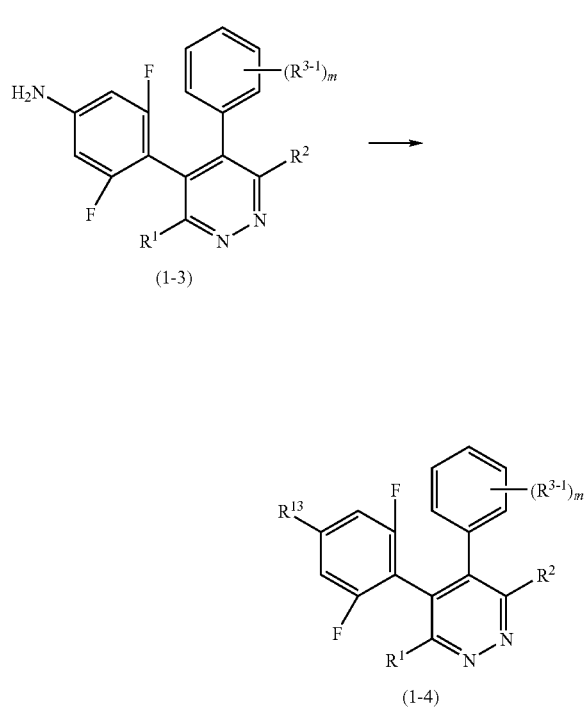

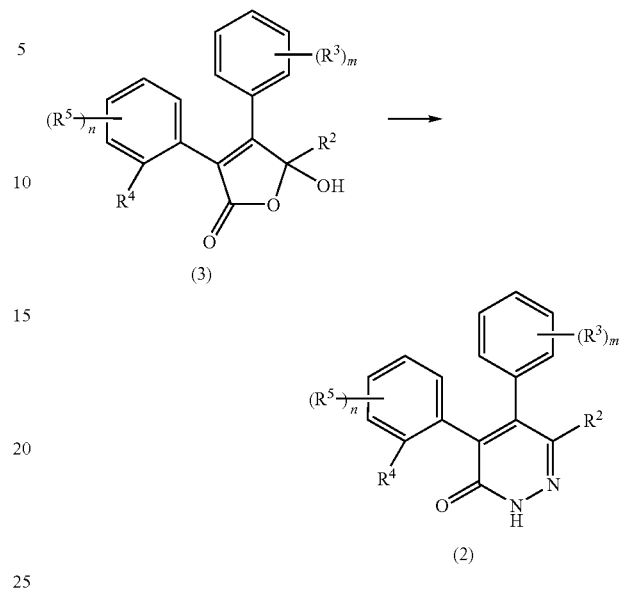

(wherein, $R^2$, $R^3$, m, $R^4$, $R^5$ and n are the same meanings as described above).

The compound represented by the formula (2) an be produced by reacting the compound represented by the formula (3) with hydrazine.

The reaction is carried out usually in a solvent.

The solvent used in the reaction includes, for example, alcohols such as methanol, ethanol, propanol, isopropanol, butanol and the like, ethers such as tetrahydrofuran, 1,2-dimethoxyethane and the like, and mixtures thereof.

The amount of hydrazine used in the reaction is usually a proportion of 1 to 5 mol per 1 mol of the compound represented by the formula (3). Hydrazine used in the reaction may be its hydrate.

The reaction temperature is usually in a range of 0 to 120° C., and the reaction time is usually in a range of 1 to 24 hours.

After completion of the reaction, the compound represented by the formula (2) can be isolated by subjecting to a post treatment operation such as cooling the reaction mixture to deposit solid which is then filtrated, or subjecting the reaction mixture to concentrate and the like. The compound represented by the formula (2) isolated can also be further purified by chromatography, re-crystallization and the like.

(wherein, $R^2$ and m are the same meanings as described above, $R^1$ is a chlorine atom, a bromine atom or a C1-C4 alkoxy group, $R^{3-1}$ is a halogen atom, a cyano group, a C1-C4 alkyl group optionally substituted by at least one halogen atom, a C1-C4 alkoxy group optionally substituted by at least one halogen atom, or a C1-C4 alkylthio group optionally substituted by at least one halogen atom, and $R^{13}$ is a chlorine atom or a bromine atom.).

The reaction is carried out usually in a solvent.

Examples of the solvent used in the reaction include acetonitrile, propionitrile and the like. The alkyl nitrite used in the reaction includes, for example, tert-butyl nitrite and isoamyl nitrite, and the copper halide (II) includes, for example, copper chloride (II) and copper bromide (II), and these are selected depending on the kind of $R^{13}$ of the compound represented by the formula (1-4).

The amounts of the alkyl nitrite and the copper halide (II) used in the reaction are each usually a proportion of 1 to 2 mol per 1 mol of the compound represented by the formula (1-3).

The reaction temperature is usually in a range of 0 to 50° C., and the reaction time is usually in a range of 1 to 24 hours.

After completion of the reaction, for example, the reaction mixture is subjected to a post treatment operation such as water being added to the reaction mixture and extracting with an organic solvent, and the resulting organic layer being dried, concentration and the like; thus, the compound represented by the formula (1-4) can be isolated. The compound represented by the formula (1-4) isolated can also be further purified by chromatography, re-crystallization and the like.

Next, examples of production of intermediates of the compound of the present invention will be shown as Reference Production Methods.

(Reference Production Method 2)

The compound represented by the formula (3) can be produced according to the following scheme.

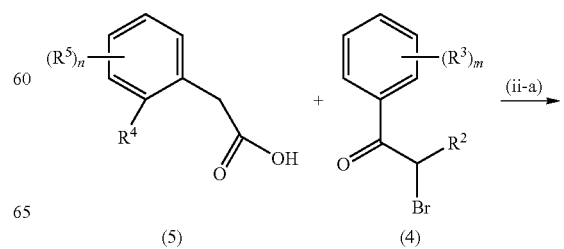

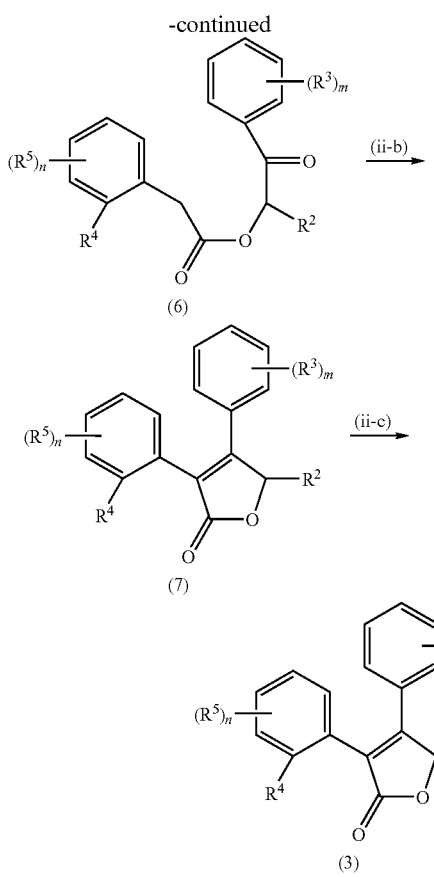

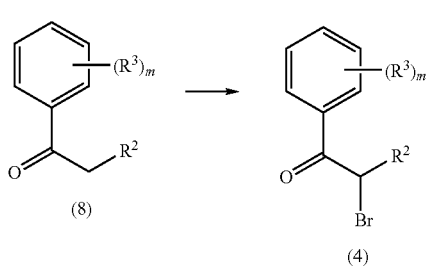

(wherein, $R^2$, $R^3$, m, $R^4$, $R^5$ and n are the same meanings as described above).

The production method shown in the above-mentioned scheme is composed of a process (ii-a), process (ii-b) and process (ii-c).

The reaction in the process (ii-a) can be carried out, for example, by mixing the compound represented by the formula (4); the compound represented by the formula (5); an acyclic tertiary amine such as triethylamine, diisopropylethylamine and the like; and a solvent.

The solvent used in the reaction includes, for example, nitrites such as acetonitrile, propionitrile and the like.

Regarding the amount of the reagent used in the reaction, the proportion of the compound represented by the formula (5) is usually 0.8 to 1.3 mol and the proportion of a weak base is usually 0.8 to 1.3 mol, per 1 mol of the compound represented by the formula (4).

The reaction temperature is usually in a range of 0 to 50° C., and the reaction time is usually in a range of 1 to 48 hours.

After completion of the reaction, the reaction mixture can be used itself in the reaction of the process (ii-b).

The reaction of the process (ii-b) can be carried out, for example, by mixing the reaction mixture obtained by the reaction of the process (ii-a) with at least one cyclic amine compound selected from 1,8-diazabicyclo[5.4.0]undec-7-ene (DBU), 1,5-diazabicyclo[4.3.0]non-5-ene (DBN) and 1,4-diazabicyclo[2.2.2]octane (triethylenediamine).

The amount of the cyclic amine compound used in the reaction is usually a proportion of 1 to 3 mol per 1 mol of the compound represented by the formula (6).

The reaction temperature is usually in a range of −20 to 50° C., and the reaction time is usually in a range of 1 to 8 hours.

After completion of the reaction, the reaction mixture can be used as it is in the reaction of the process (ii-c).

The reaction of the process (ii-c) can be carried out, for example, by blowing a gas containing oxygen into the reaction mixture obtained by the reaction of the process (ii-b).

The gas containing oxygen used in this reaction includes, for example, oxygen and air.

The reaction temperature is usually in a range of 0 to 50° C., and the reaction time is usually in a range of 1 to 24 hours.

After completion of the reaction of the process (ii-c), the reaction mixture is subjected to a post treatment operation such as dilute hydrochloric acid being added to the reaction mixture and extracting with an organic solvent, and the resulting organic layer being dried, concentration and the like; thus, the compound represented by the formula (3) can be isolated. The compound represented by the formula (3) isolated can also be further purified by chromatography, re-crystallization and the like.

(Reference Production Method 3)

(wherein, $R^2$, $R^3$ and m are the same meanings as described above)

The compound represented by the formula (4) can be produced by reacting the compound represented by the formula (8) with bromine.

The reaction is carried out usually in a solvent.

The solvent used in the reaction includes, for example, acetic acid.

The amount of bromine used in the reaction is usually a proportion of 0.8 to 1.3 mol per 1 mol of the compound represented by the formula (8).

The reaction temperature is usually in a range of −10 to 40° C., and the reaction time is usually in a range of 0.1 to 24 hours.

The reaction can also be carried out in the presence of catalytic amount of hydrobromic acid.

After completion of the reaction, the reaction mixture is subjected to a post treatment operation such as the reaction mixture being concentrated, or water being added to the reaction mixture and extracting with an organic solvent, the organic layer being washed by a sodium hydrogen carbonate aqueous solution and water, and being dried, concentration and the like is carried out; thus, the compound represented by the formula (4) can be isolated. The compound represented by the formula (4) isolated can also be further purified by chromatography, re-crystallization and the like.

(Reference Production Method 4)

The compound represented by the formula (1-3) can be produced by subjecting the compound represented by the formula (1-5) to a reduction reaction.

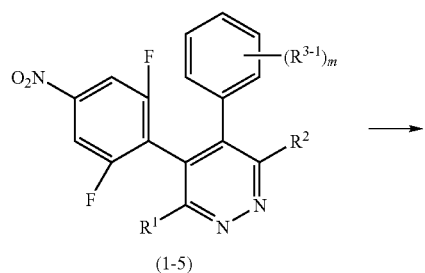

(1-5)

→

Pyridazine compound represented by the formula (1-b)

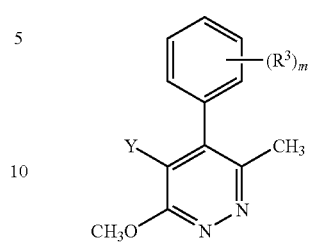

(1-b)

In the formula (1-a) or (1-b), $(R^3)_m$ and Y represent one combination of substituents shown in Table 1.

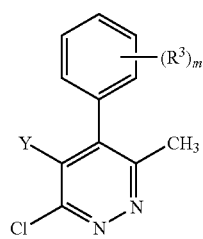

(1-3)

(wherein, $R^1$, $R^2$, $R^{3-1}$ and m are the same meanings as described above).

The reaction is carried out, for example, in a mixed solvent of water, acetic acid and ethyl acetate in the presence of iron.

The amount of iron used in the reaction is usually a proportion of 4 to 10 mol per 1 mol of the compound represented by the formula (1-5).

The reaction temperature is usually in a range of 20 to 100° C., and the reaction time is usually in a range of 0.1 to 24 hours.

After completion of the reaction, the reaction mixture is subjected to a post treatment operation such as water being added to the reaction mixture and extracting with an organic solvent, and the organic layer being dried, concentration and the like, thus, the compound represented by the formula (1-3) can be isolated. The compound represented by the formula (1-3) isolated can also be further purified by chromatography, re-crystallization and the like.

Next, specific examples of the compound of the present invention will be shown.

Pyridazine compound represented by the formula (1-a)

(1-a)

TABLE 1

| $(R^3)_m$ | Y |
|---|---|
| 4-$CH_3$ | 2,4,6-trifluorophenyl |
| 3-$CH_3$ | 2,4,6-trifluorophenyl |
| 2-$CH_3$ | 2,4,6-trifluorophenyl |
| 4-$CF_3$ | 2,4,6-trifluorophenyl |
| 4-Cl | 2,4,6-trifluorophenyl |
| 3-Cl | 2,4,6-trifluorophenyl |
| 2-Cl | 2,4,6-trifluorophenyl |
| 4-F | 2,4,6-trifluorophenyl |
| 4-$NO_2$ | 2,4,6-trifluorophenyl |
| 4-CN | 2,4,6-trifluorophenyl |
| 4-$OCH_3$ | 2,4,6-trifluorophenyl |
| 4-$OCF_3$ | 2,4,6-trifluorophenyl |
| 4-$OCHF_2$ | 2,4,6-trifluorophenyl |
| 4-$OCClF_2$ | 2,4,6-trifluorophenyl |
| 4-$OCBrF_2$ | 2,4,6-trifluorophenyl |
| 4-$SCH_3$ | 2,4,6-trifluorophenyl |
| 4-$SCF_3$ | 2,4,6-trifluorophenyl |
| — | 2,4,6-trifluorophenyl |
| 4-$CH_3$ | 2-chlorophenyl |
| 4-Cl | 2-chlorophenyl |
| 4-$CH_3$ | 2-fluorophenyl |
| 4-Cl | 2-fluorophenyl |
| 2-Cl,4-Cl | 2,4,6-trifluorophenyl |
| 3-Cl,4-Cl | 2,4,6-trifluorophenyl |
| 2-$CH_3$,4-$CH_3$ | 2,4,6-trifluorophenyl |
| 3-$CH_3$,4-$CH_3$ | 2,4,6-trifluorophenyl |
| 3-$OCH_3$,4-$OCH_3$ | 2,4,6-trifluorophenyl |
| 2-F,4-F | 2,4,6-trifluorophenyl |
| 2-F,4-Cl | 2,4,6-trifluorophenyl |
| 4-$CH_3$ | 2-nitrophenyl |
| 4-Cl | 2-nitrophenyl |
| 4-$CH_3$ | 2-cyanophenyl |
| 4-Cl | 2-cyanophenyl |
| 4-$CH_3$ | 2-chloro-6-fluorophenyl |
| 4-$CF_3$ | 2-chloro-6-fluorophenyl |
| 4-Cl | 2-chloro-6-fluorophenyl |
| 4-F | 2-chloro-6-fluorophenyl |
| 4-$OCH_3$ | 2-chloro-6-fluorophenyl |
| 2-Cl,4-Cl | 2-chloro-6-fluorophenyl |
| 3-Cl,4-Cl | 2-chloro-6-fluorophenyl |
| 2-$CH_3$,4-$CH_3$ | 2-chloro-6-fluorophenyl |
| 3-$CH_3$,4-$CH_3$ | 2-chloro-6-fluorophenyl |
| 2-F,4-F | 2-chloro-6-fluorophenyl |
| 2-F,4-Cl | 2-chloro-6-fluorophenyl |
| 4-$CH_3$ | 2,6-difluoro-4-methoxyphenyl |
| 4-$CF_3$ | 2,6-difluoro-4-methoxyphenyl |
| 4-Cl | 2,6-difluoro-4-methoxyphenyl |
| 4-F | 2,6-difluoro-4-methoxyphenyl |
| 4-$OCH_3$ | 2,6-difluoro-4-methoxyphenyl |
| 2-Cl,4-Cl | 2,6-difluoro-4-methoxyphenyl |
| 3-Cl,4-Cl | 2,6-difluoro-4-methoxyphenyl |
| 2-$CH_3$,4-$CH_3$ | 2,6-difluoro-4-methoxyphenyl |
| 3-$CH_3$,4-$CH_3$ | 2,6-difluoro-4-methoxyphenyl |
| 2-F,4-F | 2,6-difluoro-4-methoxyphenyl |
| 2-F,4-Cl | 2,6-difluoro-4-methoxyphenyl |
| 4-$CH_3$ | 2,6-difluoro-4-ethoxyphenyl |
| 4-Cl | 2,6-difluoro-4-ethoxyphenyl |

TABLE 1-continued

| (R³)ₘ | Y |
|---|---|
| 4-CH₃ | 2-methylphenyl |
| 4-Cl | 2-methylphenyl |
| 4-CH₃ | 2-(trifluoromethyl)phenyl |
| 4-Cl | 2-(trifluoromethyl)phenyl |
| 4-CH₃ | 2,6-difluorophenyl |
| 3-CH₃ | 2,6-difluorophenyl |
| 2-CH₃ | 2,6-difluorophenyl |
| 4-CF₃ | 2,6-difluorophenyl |
| 4-Cl | 2,6-difluorophenyl |
| 3-Cl | 2,6-difluorophenyl |
| 2-Cl | 2,6-difluorophenyl |
| 4-F | 2,6-difluorophenyl |
| 4-NO₂ | 2,6-difluorophenyl |
| 4-CN | 2,6-difluorophenyl |
| 4-OCH₃ | 2,6-difluorophenyl |
| 4-OCF₃ | 2,6-difluorophenyl |
| 4-OCHF₂ | 2,6-difluorophenyl |
| 4-OCClF₂ | 2,6-difluorophenyl |
| 4-OCBrF₂ | 2,6-difluorophenyl |
| 4-SCH₃ | 2,6-difluorophenyl |
| 4-SCF₃ | 2,6-difluorophenyl |
| — | 2,6-difluorophenyl |
| 2-Cl,4-Cl | 2,6-difluorophenyl |
| 3-Cl,4-Cl | 2,6-difluorophenyl |
| 2-Cl,4-CH₃ | 2,6-difluorophenyl |
| 3-CH₃,4-CH₃ | 2,6-difluorophenyl |
| 3-OCH₃,4-OCH₃ | 2,6-difluorophenyl |
| 2-F,4-F | 2,6-difluorophenyl |
| 2-F,4-Cl | 2,6-difluorophenyl |
| 4-CH₃ | 2,4-difluorophenyl |
| 4-CF₃ | 2,4-difluorophenyl |
| 4-Cl | 2,4-difluorophenyl |
| 4-F | 2,4-difluorophenyl |
| 4-OCH₃ | 2,4-difluorophenyl |
| 2-Cl,4-Cl | 2,4-difluorophenyl |
| 3-Cl,4-Cl | 2,4-difluorophenyl |
| 2-CH₃,4-CH₃ | 2,4-difluorophenyl |
| 3-CH₃,4-CH₃ | 2,4-difluorophenyl |
| 2-F,4-F | 2,4-difluorophenyl |
| 2-F,4-Cl | 2,4-difluorophenyl |
| 4-CH₃ | 2,3,4-trifluorophenyl |
| 4-Cl | 2,3,4-trifluorophenyl |
| 4-CH₃ | 2,3,5-trifluorophenyl |
| 4-Cl | 2,3,5-trifluorophenyl |
| 4-CH₃ | 2,3,6-trifluorophenyl |
| 4-Cl | 2,3,6-trifluorophenyl |
| 4-CH₃ | 2,4,5-trifluorophenyl |
| 4-Cl | 2,3,5-trifluorophenyl |
| 4-CH₃ | 2,3-difluorophenyl |
| 4-Cl | 2,3-difluorophenyl |
| 4-CH₃ | 2,5-difluorophenyl |
| 4-Cl | 2,5-difluorophenyl |
| 4-CH₃ | 2-(difluoromethoxy)phenyl |
| 4-Cl | 2-(difluoromethoxy)phenyl |
| 4-CH₃ | 2-(trifluoromethoxy)phenyl |
| 4-Cl | 2-(trifluoromethoxy)phenyl |
| 4-CH₃ | 2-methoxyphenyl |
| 4-Cl | 2-methoxyphenyl |
| 4-Cl | pentafluorophenyl |
| 4-Cl | 4-methoxy-2,3,5,6-tetrafluorophenyl |
| 4-Cl | 4-ethoxy-2,3,5,6-tetrafluorophenyl |
| 4-Cl | 4-cyano-2,3,5,6-tetrafluorophenyl |
| 4-Cl | 4-nitro-2,3,5,6-tetrafluorophenyl |
| 4-Cl | 2,3,5,6-tetrafluorophenyl |
| 4-Cl | 2,6-difluoro-4-cyanophenyl |
| 4-Cl | 2,6-difluoro-4-nitrophenyl |
| 4-Cl | 2,6-difluoro-4-chlorophenyl |
| 4-Cl | 2,6-difluoro-4-(trifluoromethyl)phenyl |
| 4-Cl | 2-fluoro-6-methylphenyl |
| 4-Cl | 2-fluoro-6-nitrophenyl |
| 4-Cl | 2-cyano-6-fluorophenyl |
| 4-Cl | 2-fluoro-6-(trifluoromethyl)phenyl |
| 4-Cl | 2-(difluoromethoxy)-6-fluorophenyl |
| 4-Cl | 2-fluoro-6-(trifluoromethoxy)phenyl |
| 4-Cl | 2-fluoro-6-methoxyphenyl |

TABLE 1-continued

| (R³)ₘ | Y |
|---|---|
| 4-Cl | 2,3-difluoro-6-(trifluoromethyl)phenyl |
| 4-Cl | 2,6-difluoro-3-chlorophenyl |

In the table, "—" means that m is 0.

Next, specific examples of the intermediate of the compound of the present invention will be shown below.

The compound represented by the formula (2-a):

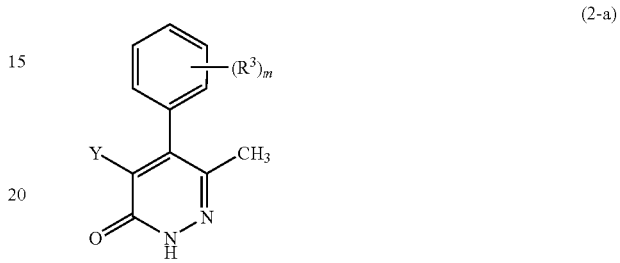

(2-a)

The compound represented by the formula (3-a):

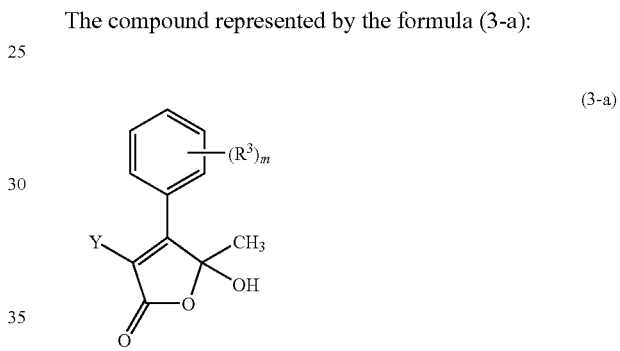

(3-a)

The compound represented by the formula (6-a):

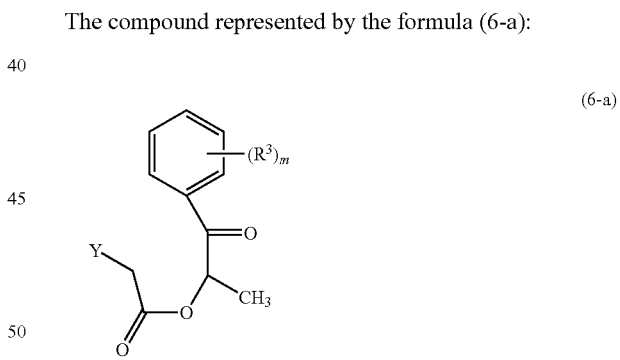

(6-a)

The compound represented by the formula (7-a):

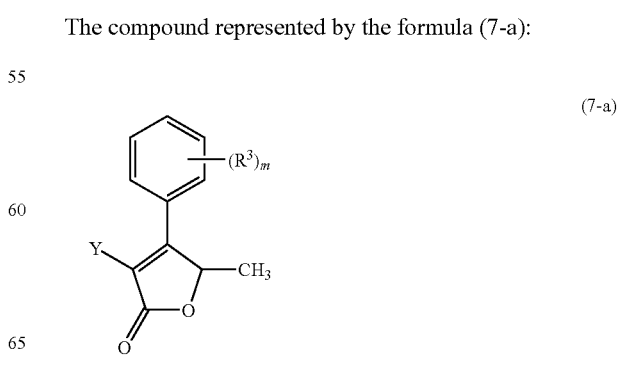

(7-a)

In the formula (2-a), (3-a), (6-a) or (7-a), $(R^3)_m$ and Y represent one combination of substituents shown in Table 2.

TABLE 2

| $(R^3)_m$ | Y |
|---|---|
| 4-CH$_3$ | 2,4,6-trifluorophenyl |
| 3-CH$_3$ | 2,4,6-trifluorophenyl |
| 2-CH$_3$ | 2,4,6-trifluorophenyl |
| 4-CF$_3$ | 2,4,6-trifluorophenyl |
| 4-Cl | 2,4,6-trifluorophenyl |
| 3-Cl | 2,4,6-trifluorophenyl |
| 2-Cl | 2,4,6-trifluorophenyl |
| 4-F | 2,4,6-trifluorophenyl |
| 4-NO$_2$ | 2,4,6-trifluorophenyl |
| 4-CN | 2,4,6-trifluorophenyl |
| 4-OCH$_3$ | 2,4,6-trifluorophenyl |
| 4-OCF$_3$ | 2,4,6-trifluorophenyl |
| 4-OCHF$_2$ | 2,4,6-trifluorophenyl |
| 4-OCClF$_2$ | 2,4,6-trifluorophenyl |
| 4-OCBrF$_2$ | 2,4,6-trifluorophenyl |
| 4-SCH$_3$ | 2,4,6-trifluorophenyl |
| 4-SCF$_3$ | 2,4,6-trifluorophenyl |
| — | 2,4,6-trifluorophenyl |
| 4-CH$_3$ | 2-chlorophenyl |
| 4-Cl | 2-chlorophenyl |
| 4-CH$_3$ | 2-fluorophenyl |
| 4-Cl | 2-fluorophenyl |
| 2-Cl,4-Cl | 2,4,6-trifluorophenyl |
| 3-Cl,4-Cl | 2,4,6-trifluorophenyl |
| 2-CH$_3$,4-CH$_3$ | 2,4,6-trifluorophenyl |
| 3-CH$_3$,4-CH$_3$ | 2,4,6-trifluorophenyl |
| 3-OCH$_3$,4-OCH$_3$ | 2,4,6-trifluorophenyl |
| 2-F,4-F | 2,4,6-trifluorophenyl |
| 2-F,4-Cl | 2,4,6-trifluorophenyl |
| 4-CH$_3$ | 2-chloro-6-fluorophenyl |
| 4-CF$_3$ | 2-chloro-6-fluorophenyl |
| 4-Cl | 2-chloro-6-fluorophenyl |
| 4-F | 2-chloro-6-fluorophenyl |
| 4-OCH$_3$ | 2-chloro-6-fluorophenyl |
| 2-Cl,4-Cl | 2-chloro-6-fluorophenyl |
| 3-Cl,4-Cl | 2-chloro-6-fluorophenyl |
| 2-CH$_3$,4-CH$_3$ | 2-chloro-6-fluorophenyl |
| 3-CH$_3$,4-CH$_3$ | 2-chloro-6-fluorophenyl |
| 2-F,4-F | 2-chloro-6-fluorophenyl |
| 2-F,4-Cl | 2-chloro-6-fluorophenyl |
| 4-CH$_3$ | 2-methylphenyl |
| 4-Cl | 2-methylphenyl |
| 4-CH$_3$ | 2-(trifluoromethyl)phenyl |
| 4-Cl | 2-(trifluoromethyl)phenyl |
| 4-CH$_3$ | 2,6-difluoro-4-methoxyphenyl |
| 4-CF$_3$ | 2,6-difluoro-4-methoxyphenyl |
| 4-Cl | 2,6-difluoro-4-methoxyphenyl |
| 4-F | 2,6-difluoro-4-methoxyphenyl |
| 4-OCH$_3$ | 2,6-difluoro-4-methoxyphenyl |
| 2-Cl,4-Cl | 2,6-difluoro-4-methoxyphenyl |
| 3-Cl,4-Cl | 2,6-difluoro-4-methoxyphenyl |
| 2-CH$_3$,4-CH$_3$ | 2,6-difluoro-4-methoxyphenyl |
| 3-CH$_3$,4-CH$_3$ | 2,6-difluoro-4-methoxyphenyl |
| 2-F,4-F | 2,6-difluoro-4-methoxyphenyl |
| 2-F,4-Cl | 2,6-difluoro-4-methoxyphenyl |
| 4-CH$_3$ | 2,6-difluoro-4-ethoxyphenyl |
| 4-Cl | 2,6-difluoro-4-ethoxyphenyl |
| 4-CH$_3$ | 2-nitrophenyl |
| 4-Cl | 2-nitrophenyl |
| 4-CH$_3$ | 2-cyanophenyl |
| 4-Cl | 2-cyanophenyl |
| 4-CH$_3$ | 2,6-difluorophenyl |
| 3-CH$_3$ | 2,6-difluorophenyl |
| 2-CH$_3$ | 2,6-difluorophenyl |
| 4-CF$_3$ | 2,6-difluorophenyl |
| 4-Cl | 2,6-difluorophenyl |
| 3-Cl | 2,6-difluorophenyl |
| 2-Cl | 2,6-difluorophenyl |
| 4-F | 2,6-difluorophenyl |
| 4-NO$_2$ | 2,6-difluorophenyl |
| 4-CN | 2,6-difluorophenyl |
| 4-OCH$_3$ | 2,6-difluorophenyl |
| 4-OCF$_3$ | 2,6-difluorophenyl |
| 4-OCHF$_2$ | 2,6-difluorophenyl |

TABLE 2-continued

| $(R^3)_m$ | Y |
|---|---|
| 4-OCClF$_2$ | 2,6-difluorophenyl |
| 4-OCBrF$_2$ | 2,6-difluorophenyl |
| 4-SCH$_3$ | 2,6-difluorophenyl |
| 4-SCF$_3$ | 2,6-difluorophenyl |
| — | 2,6-difluorophenyl |
| 2-Cl,4-Cl | 2,6-difluorophenyl |
| 3-Cl,4-Cl | 2,6-difluorophenyl |
| 2-Cl,4-CH$_3$ | 2,6-difluorophenyl |
| 3-CH$_3$,4-CH$_3$ | 2,6-difluorophenyl |
| 3-OCH$_3$,4-OCH$_3$ | 2,6-difluorophenyl |
| 2-F,4-F | 2,6-difluorophenyl |
| 2-F,4-Cl | 2,6-difluorophenyl |
| 4-CH$_3$ | 2,4-difluorophenyl |
| 4-CF$_3$ | 2,4-difluorophenyl |
| 4-Cl | 2,4-difluorophenyl |
| 4-F | 2,4-difluorophenyl |
| 4-OCH$_3$ | 2,4-difluorophenyl |
| 2-Cl,4-Cl | 2,4-difluorophenyl |
| 3-Cl,4-Cl | 2,4-difluorophenyl |
| 2-CH$_3$,4-CH$_3$ | 2,4-difluorophenyl |
| 3-CH$_3$,4-CH$_3$ | 2,4-difluorophenyl |
| 2-F,4-F | 2,4-difluorophenyl |
| 2-F,4-Cl | 2,4-difluorophenyl |
| 4-CH$_3$ | 2,3,4-trifluorophenyl |
| 4-Cl | 2,3,4-trifluorophenyl |
| 4-CH$_3$ | 2,3,5-trifluorophenyl |
| 4-Cl | 2,3,5-trifluorophenyl |
| 4-CH$_3$ | 2,3,6-trifluorophenyl |
| 4-Cl | 2,3,6-trifluorophenyl |
| 4-CH$_3$ | 2,3,5-trifluorophenyl |
| 4-Cl | 2,3,5-trifluorophenyl |
| 4-CH$_3$ | 2,3-difluorophenyl |
| 4-Cl | 2,3-difluorophenyl |
| 4-CH$_3$ | 2,5-difluorophenyl |
| 4-Cl | 2,5-difluorophenyl |
| 4-CH$_3$ | 2-(difluoromethoxy)phenyl |
| 4-Cl | 2-(difluoromethoxy)phenyl |
| 4-CH$_3$ | 2-(trifluoromethoxy)phenyl |
| 4-Cl | 2-(trifluoromethoxy)phenyl |
| 4-CH$_3$ | 2-methoxyphenyl |
| 4-Cl | 2-methoxyphenyl |
| 4-Cl | pentafluorophenyl |
| 4-Cl | 4-methoxy-2,3,5,6-tetrafluorophenyl |
| 4-Cl | 4-ethoxy-2,3,5,6-tetrafluorophenyl |
| 4-Cl | 4-cyano-2,3,5,6-tetrafluorophenyl |
| 4-Cl | 4-nitro-2,3,5,6-tetrafluorophenyl |
| 4-Cl | 2,3,5,6-tetrafluorophenyl |
| 4-Cl | 2,6-difluoro-4-cyanophenyl |
| 4-Cl | 2,6-difluoro-4-nitrophenyl |
| 4-Cl | 2,6-difluoro-4-chlorophenyl |
| 4-Cl | 2,6-difluoro-4-(trifluoromethyl)phenyl |
| 4-Cl | 2-fluoro-6-methylphenyl |
| 4-Cl | 2-fluoro-6-nitrophenyl |
| 4-Cl | 2-cyano-6-fluorophenyl |
| 4-Cl | 2-fluoro-6-(trifluoromethyl)phenyl |
| 4-Cl | 2-(difluoromethoxy)-6-fluorophenyl |
| 4-Cl | 2-fluoro-6-(trifluoromethoxy)phenyl |
| 4-Cl | 2-fluoro-6-methoxyphenyl |
| 4-Cl | 2,3-difluoro-6-(trifluoromethyl)phenyl |
| 4-Cl | 2,6-difluoro-3-chlorophenyl |

In the table, "—" means that m is 0.

The compound represented by the formula (4-a):

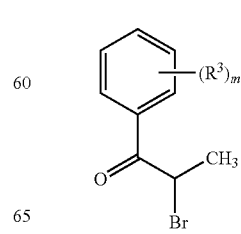

(4-a)

The compound represented by the formula (8-a):

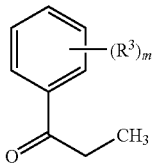

(8-a)

In the formula (4-a) or (8-a), $(R^3)_m$ represents one of substituent shown in Table 3.

TABLE 3

| $(R^3)_m$ |
|---|
| 4-CH$_3$ |
| 3-CH$_3$ |
| 2-CH$_3$ |
| 4-CF$_3$ |
| 4-Cl |
| 3-Cl |
| 2-Cl |
| 4-F |
| 4-NO$_2$ |
| 4-CN |
| 4-OCH$_3$ |
| 4-OCF$_3$ |
| 4-OCHF$_2$ |
| 4-OCClF$_2$ |
| 4-OCBrF$_2$ |
| 4-SCH$_3$ |
| 4-SCF$_3$ |
| — |
| 2-Cl,4-Cl |
| 3-Cl,4-Cl |
| 2-CH$_3$,4-CH$_3$ |
| 3-CH$_3$,4-CH$_3$ |
| 3-OCH$_3$,4-OCH$_3$ |
| 2-F,4-F |
| 2-F,4-Cl |

In the table, "—" means that m is 0.

The compound represented by the formula (5-a):

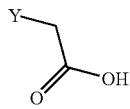

(5-a)

In the formula (5-a), Y represents one of substituent shown in Table 4.

TABLE 4

| Y |
|---|
| 2,4,6-trifluorophenyl |
| 2-chloro-6-fluorophenyl |
| 2,6-difluoro-4-methoxyphenyl |
| 2,6-difluoro-4-ethoxyphenyl |
| 2,6-difluorophenyl |
| 2,4-difluorophenyl |
| 2,3,4-trifluorophenyl |
| 2,3,5-trifluorophenyl |
| 2,3,6-trifluorophenyl |
| 2,4,5-trifluorophenyl |
| 2,3-difluorophenyl |
| 2,5-difluorophenyl |
| 2-chlorophenyl |

TABLE 4-continued

| Y |
|---|
| 2-fluorophenyl |
| 2-nitrophenyl |
| 2-cyanophenyl |
| 2-methylphenyl |
| 2-(trifluoromethyl)phenyl |
| 2-(difluoromethoxy)phenyl |
| 2-(trifluoromethoxy)phenyl |
| 2-methoxyphenyl |
| pentafluorophenyl |
| 4-methoxy-2,3,5,6-tetrafluorophenyl |
| 4-ethoxy-2,3,5,6-tetrafluorophenyl |
| 4-cyano-2,3,5,6-tetrafluorophenyl |
| 4-nitro-2,3,5,6-tetrafluorophenyl |
| 2,3,5,6-tetrafluorophenyl |
| 2,6-difluoro-4-cyanophenyl |
| 2,6-difluoro-4-nitrophenyl |
| 2,6-difluoro-4-chlorophenyl |
| 2,6-difluoro-4-(trifluoromethyl)phenyl |
| 2-fluoro-6-methylphenyl |
| 2-fluoro-6-nitrophenyl |
| 2-cyano-6-fluorophenyl |
| 2-fluoro-6-(trifluoromethyl)phenyl |
| 2-(difluoromethoxy)-6-fluorophenyl |
| 2-fluoro-6-(trifluoromethoxy)phenyl |
| 2-fluoro-6-methoxyphenyl |
| 2,3-difluoro-6-(trifluoromethyl)phenyl |
| 2,6-difluoro-3-chlorophenyl |

The plant diseases to be controlled by the present compound will be exemplified below.

*Pyricularia oryzae, Cochliobolus miyabeanus* and *Rhizoctonia solani* of rice;

*Erysiphe graminis, Gibberella zeae, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici* and *Leptosphaeria nodorum*, of wheat and barley; *Diaporthe citri, Elsinoe fawcetti, Penicillium digitatum* and *P. italicum* of citrus;

*Sclerotinia mali, Valsa mali, Podosphaera leucotricha, Alternaria mali* and *Venturia inaequalis* of apple;

*Venturia nashicola, V. pirina, Alternaria kikuchiana* and *Gymnosporangium haraeanum* of pear; *Sclerotinia cinerea, Cladosporium carpophilum* and *Phomopsis* sp. of peach;

*Elsinoe ampelina, Glomerella cingulata, Uncinula necator, Phakopsora ampelopsidis, Guignardia bidwellii* and *Plasmopara viticola*, of grape;

*Gloeosporium kaki, Cercospora kaki* and *Mycosphaerella nawae* of Japanese persimmon;

*Colletotrichum lagenarium, Sphaerotheca fuliginea, Mycosphaerella melonis, Fusarium oxysporum, Pseudoperonospora cubensis Phytophthora* sp. and *Pythium* sp. of cucurbit;

*Alternaria solani, Cladosporium fulvum* and *Phytophthora infestans* of tomato;

*Phomopsis vexans* and *Erysiphe cichoracearum*, of eggplant;

*Alternaria japonica* and *Cercosporella brassicae* of Cruciferae vegetables;

*Puccinia allii* of green onion; *Cercospora kikuchii, Elsinoe glycines* and *Diaporthe phaseolorum* var. *sojae* of soybean; *Colletotrichum lindemthianum* of kidney bean;

*Cercospora personata* and *Cercospora arachidicola* of peanut; *Erysiphe pisi* of pea;

*Alternaria solani* and *Phytophthora infestans* of potato;

*Sphaerotheca humuli* of strawberry; *Exobasidium reticulatum* and *Elsinoe leucospila* of tea;

*Alternaria longipes, Erysiphe cichoracearum, Colletotrichum tabacum, Peronospora tabacina* and *Phytophthora nicotianae* of tobacco;
*Cercospora beticola* of sugar beet;
*Diplocarpon rosae* and *Sphaerotheca pannosa* of rose; *Septoria chrysanthemi-indici* and *Puccinia horiana* of chrysanthemum;
*Botrytis cinerea* and *Sclerotinia sclerotiorum* of various crops; *Alternaria brassicicola* of radish;
and *Sclerotinia homeocarpa* and *Rhizoctonia solani* of turf.

Fungicidal effect may be shown by treating the compound of the present invention as it is to plants or soils. But, usually, it is used by the form of composition comprising the compound of the present invention and a carrier. Namely, the fungicidal composition of the present invention is formulated to an emulsifiable concentrate, a wettable powder, a water dispersible granule, a flowable, a dust, a granule and the like by mixing the compound of the present invention and a solid carrier and/or a liquid carrier and, if necessary, adding other adjuvant for formulation such as surfactant.

These formulations usually contain 0.1 to 90% by weight of the compound of the present invention.

Solid carriers used for formulation include, for example, fine powders or granules of minerals such as kaolin clay, attapulgite clay, bentonite, montmorillonite, terra alba, pyrophyllite, talc, diatomaceous earth, calcite and the like; natural organic substances such as corncob powder, walnut shell powder and the like; synthetic organic substances such as urea and the like; salts such as calcium carbonate, ammonium sulfate and the like; synthetic inorganic substances such as synthetic hydrous silicon oxide and the like. Liquid carriers include, for example, aromatic hydrocarbons such as xylene, alkylbenzene, methylnaphthalene and the like; alcohols such as 2-propanol, ethylene glycol, propylene glycol, cellosolve and the like; ketones such as acetone, cyclohexanone, isophorone and the like; vegetable oils such as soybean oil, cottonseed oil and the like; aliphatic hydrocarbons, esters, dimethylsulfoxide, acetonitrile and water.

Surfactants include, for example, anionic surfactants such as alkylsulfuric acid ester salt, alkylarylsulfonic acid salt, dialkylsulfosuccinic acid salt, polyoxyethylenealkylaryletherphosphoric acid ester salt, lignin sulfonic acid salt, naphthalenesulfonate polycondensed with formaldehyde and the like; and nonionic surfactants such as polyoxyethylenealkylarylether, polyoxyethylenealkylpolyoxypropylene block copolymer, sorbitan fatty acid ester and the like.

Another adjuvant for formulation includes, for example, water-soluble polymers such as polyvinylalcohol, polyvinylpyrrolidone and the like; Arabian gum; alginic acid and its salt thereof; polysaccharides such as CMC (carboxymethylcellulose), xanthan gum and the like; inorganic substances such as aluminum magnesium silicate, alumina sol and the like; and preservatives, colorants, PAP (isopropyl acidic phosphate), stabilizing agents such as BHT and the like.

By applying the fungicidal composition of the present invention to foliage of plants, said plants can be protected from plant diseases; and by applying the fungicidal composition of the present invention to soils, the plants grown on said soils can be protected from plant diseases. Namely, the fungicidal composition of the present invention is usually used for a method for controlling plant diseases comprising a step applying an effective amount of the fungicidal composition of the present invention to plants or soils growing the plants.

When the fungicidal composition of the present invention is applied to plants or when the fungicidal composition of the present invention is applied to soil, the application amount thereof, which may be varied with a kind of control-object plants, a kind of control-object diseases, an infestation level of control-object diseases, formulation types, application timings, weather conditions and the like, is usually 1 to 5,000 g, preferably 5 to 1,000 g, of the compound of the present invention per 10,000 m$^2$.

Emulsifiable concentrate, wettable powder, flowable and the like are usually sprayed after diluted with water. In this case, the concentration of the compound of the present invention is usually in the range of from 0.0001 to 3% by weight, preferably from 0.0005 to 1% by weight. Dust, granule and the like are usually directly applied without dilution.

The fungicidal composition of the present invention can be also applied in treatment methods of seed disinfection. The methods include, for example, a method to soak seeds of a plant in the fungicidal composition of the present invention which prepared in 1 to 1,000 ppm in terms of concentration of the compound of the present invention, a method to spray or coat seeds of a plant with the fungicidal composition of the present invention which prepared in 1 to 1,000 ppm in terms of concentration of the compound of the present invention, and a method to coat seeds of a plant with the fungicidal composition of the present invention which is formulated to dust.

The method for controlling plant diseases of the present invention is usually performed by applying effective amount of the fungicidal composition of the present invention to a plant or a soil growing the plant in which infection is predictable.

The fungicidal composition of the present invention is usually used as a fungicide controlling plant diseases for agriculture or gardening, that is, as an agent controlling plant diseases to control plant diseases on plowed fields, paddy fields, orchards, tea fields, pastures, turf and the like.

The fungicidal composition of the present invention may be used together with other fungicides, insecticides, acaricides, nematicides, herbicides, plant growth regulators and/or fertilizers.

Examples of the active ingredient of the fungicides include azole fungicidal compounds such as propiconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil, flutriafol and so on; cyclic amine fungicidal compounds such as fenpropimorph, tridemorph, fenpropidin and so on; benzimidazole fungicidal compounds such as carbendazim, benomyl, thiabendazole, thiophanate-methyl and so on; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlorfluanid; folpet; kresoxim-methyl; azoxystrobin; trifloxystrobin; picoxystrobin; pyraclostrobin; N-methyl-α-methoxyimino-2-[(2,5-dimethylphenoxy)methyl]phenylacetamide; spiroxamine; quinixyfen; fenhexamide; famoxadone; fenamidone; iprovalicarb; benthiavalicarb; cyazofamid; boscalid; metrafenone and cyflufenamid.

The present invention will be illustrated further in detail by production examples, formulation examples, test examples and the like below, but the present invention is not limited to these examples.

First, production examples of the compound of the present invention will be described.

PRODUCTION EXAMPLE 1

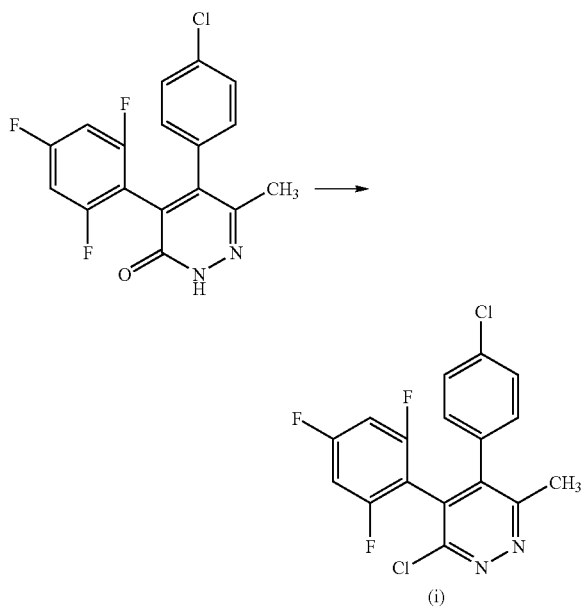

(i)

4.00 g of 5-(4-chlorophenyl)-6-methyl-4-(2,4,6-trifluorophenyl)-2H-pyridazin-3-one and 20 ml of phosphorus oxychloride were mixed and stirred at 110° C. for 1 hour. The reaction mixture was cooled down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 4.16 g of 3-chloro-5-(4-chlorophenyl)-6-methyl-4-(2,4,6-trifluorophenyl)pyridazine (hereinafter, referred to as compound (i) of the present invention).

Compound (i) of the present invention:
$^1$H-NMR (CDCl$_3$, TMS) δ (ppm): 2.54 (3H, s), 6.63 (2H, dd, J=7.3, 8.5 Hz), 7.01 (2H, d, J=8.7 Hz), 7.32 (2H, d, J=8.7 Hz)

PRODUCTION EXAMPLE 2

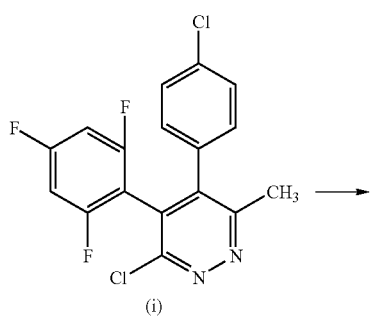

(i)

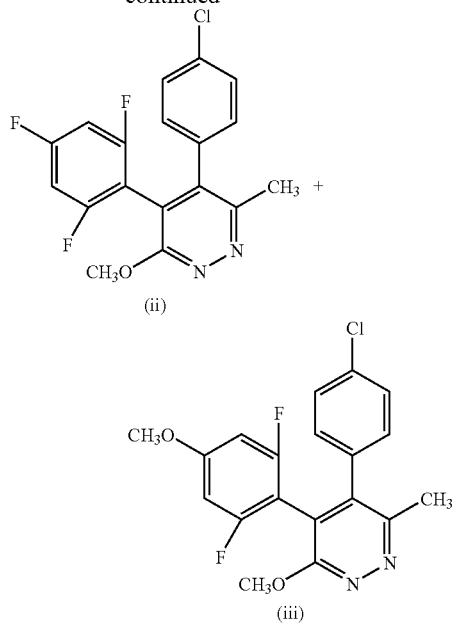

(ii)

(iii)

1.01 g of compound (i) of the present invention, 0.58 g of sodium methoxide (28% methanol solution) and 6 ml of methanol were mixed, and stirred at room temperature for 1 day, then, at 60° C. overnight. The reaction mixture was allowed to cool to room temperature. Water was poured into the reaction mixture and extracted with ethyl acetate. The organic layer was washed with water, and dried over anhydrous sodium sulfate, then, concentrated under reduced pressure. The residue was subjected to silica gel column chromatography (elution solvent: hexane-ethyl acetate), to obtain 0.32 g of 5-(4-chlorophenyl)-3-methoxy-6-methyl-4-(2,4,6-trifluorophenyl)pyridazine (hereinafter, referred to as compound (ii) of the present invention) and 89 mg of 5-(4-chlorophenyl)-4-(2,6-difluoro-4-methoxyphenyl)-3-methoxy-6-methyl-pyridazine (hereinafter, referred to as compound (iii) of the present invention), respectively.

Compound (ii) of the present invention:
$^1$H-NMR (CDCl$_3$, TMS) δ (ppm): 2.44 (3H, s), 4.11 (3H, s), 6.57 (2H, dd, J=7.3, 8.7 Hz), 7.00 (2H, d, J=8.5 Hz), 7.29 (2H, d, J=8.5 Hz)

Compound (iii) of the present invention:
$^1$H-NMR (CDCl$_3$, TMS) δ (ppm): 2.43 (3H, s), 3.75 (3H, s), 4.10 (3H, s), 6.34 (2H, d, J=9.0 Hz), 7.02 (2H, d, J=8.5 Hz), 7.28 (2H, d, J=8.5 Hz)

PRODUCTION EXAMPLE 3

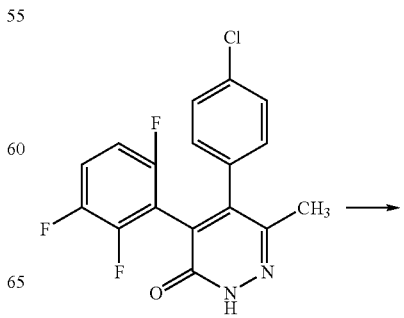

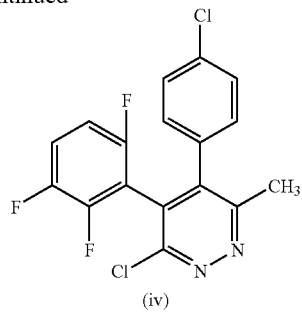

3.50 g of 5-(4-chlorophenyl)-6-methyl-4-(2,3,6-trifluorophenyl)-2H-pyridazin-3-one and 15 g of phosphorus oxychloride were mixed and stirred at 110° C. for 1 hour. The reaction mixture was cooled down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 3.68 g of 3-chloro-5-(4-chlorophenyl)-6-methyl-4-(2,3,6-trifluorophenyl)pyridazine (hereinafter, referred to as compound (iv) of the present invention).

Compound (iv) of the present invention:
$^1$H-NMR (CDCl$_3$, TMS) δ (ppm): 2.55 (3H, s), 6.75-6.85 (1H, m), 7.03 (2H, d, J=8.4 Hz), 7.1-7.2 (1H, m), 7.32 (2H, d, J=8.4 Hz)

PRODUCTION EXAMPLE 4

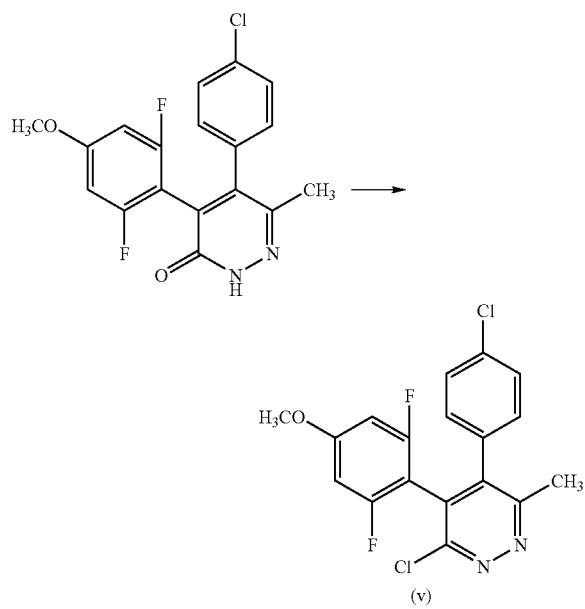

185 mg of 5-(4-chlorophenyl)-4-(2,6-difluoro-4-methoxyphenyl)-6-methyl-2H-pyridazin-3-one and 5 g of phosphorus oxychloride were mixed and stirred at 110° C. for 1 hour. The reaction mixture was allowed to cool down to room temperature and concentrated under reduced pressure. To the residue was added ethyl acetate and ice water, and separated to two layer. The organic layer was washed sequentially with water and saturated brine, and dried over anhydrous sodium sulfate, then, concentrated under reduced pressure. The residue was subjected to preparative thin layer chromatography (stationary phase: silica gel, developing solvent: hexane/ethyl acetate=3/1), to obtain 161 mg of 3-chloro-5-(4-chlorophenyl)-4-(2,6-difluoro-4-methoxyphenyl)-6-methylpyridazine (hereinafter, referred to as compound (v) of the present invention).

Compound (v) of the present invention:
$^1$H-NMR (CDCl$_3$, TMS) δ (ppm): 2.52 (3H, s), 3.77 (3H, s), 6.38 (2H, dd, J=4, 12 Hz), 7.03 (2H, d, J=8 Hz), 7.31 (2H, d, J=8 Hz)

PRODUCTION EXAMPLE 5

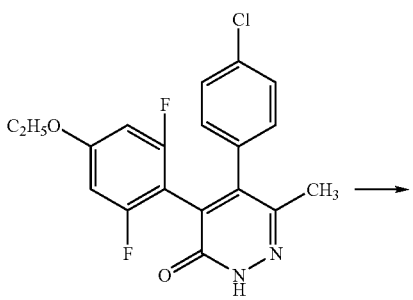

0.25 g of 5-(4-chlorophenyl)-4-(2,6-difluoro-4-ethoxyphenyl)-6-methyl-2H-pyridazin-3-one and 5 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure. The residue was subjected to preparative thin layer chromatography (stationary phase: silica gel, developing solvent: hexane/ethyl acetate=3/1), to obtain 0.16 g of 3-chloro-5-(4-chlorophenyl)-4-(2,6-difluoro-4-ethoxyphenyl)-6-methylpyridazine (hereinafter, referred to as compound (vi) of the present invention).

Compound (vi) of the present invention:
$^{1}$H-NMR (CDCl$_3$, TMS) δ (ppm): 1.40 (3H, t, J=7.2 Hz), 2.52 (3H, s), 3.96 (2H, q, J=7.2 Hz), 6.36 (2H, dd, J=5.2, 14.4 Hz), 7.02 (2H, d, J=8.8 Hz), 7.30 (2H, d, J=8.8 Hz)

PRODUCTION EXAMPLE 6

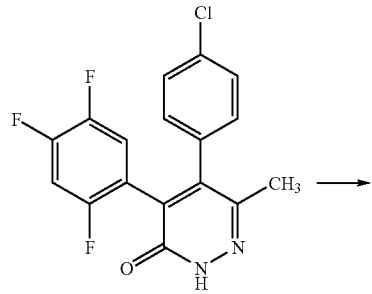

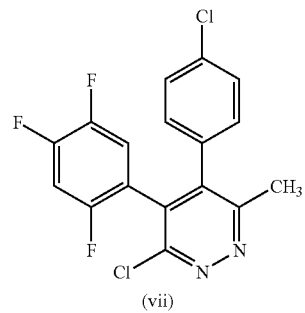

(vii)

2.09 g of 5-(4-chlorophenyl)-6-methyl-4-(2,4,5-trifluorophenyl)-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 2.10 g of 3-chloro-5-(4-chlorophenyl)-6-methyl-4-(2,4,5-trifluorophenyl)pyridazine (hereinafter, referred to as compound (vii) of the present invention).

Compound (vii) of the present invention:
$^{1}$H-NMR (CDCl$_3$, TMS) δ (ppm): 2.53 (3H, s), 6.8-6.95 (2H), 6.95-7.05 (2H, br), 7.33 (2H, d, J=8.8 Hz)

PRODUCTION EXAMPLE 7

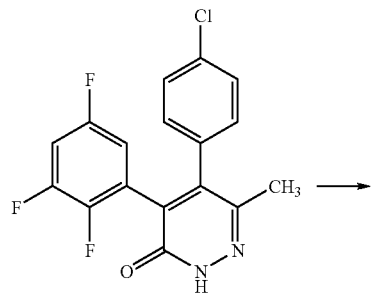

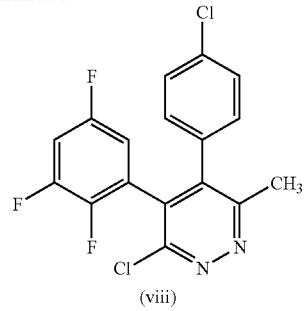

(viii)

1.80 g of 5-(4-chlorophenyl)-6-methyl-4-(2,3,5-trifluorophenyl)-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 1.83 g of 3-chloro-5-(4-chlorophenyl)-6-methyl-4-(2,3,5-trifluorophenyl)pyridazine (hereinafter, referred to as compound (viii) of the present invention).

Compound (viii) of the present invention:
$^{1}$H-NMR (CDCl$_3$, TMS) δ (ppm): 2.54 (3H, s), 6.5-6.55 (1H, m), 6.85-6.95 (1H, m), 6.95-7.05 (2H, br), 7.34 (2H, d, J=8.4 Hz)

PRODUCTION EXAMPLE 8

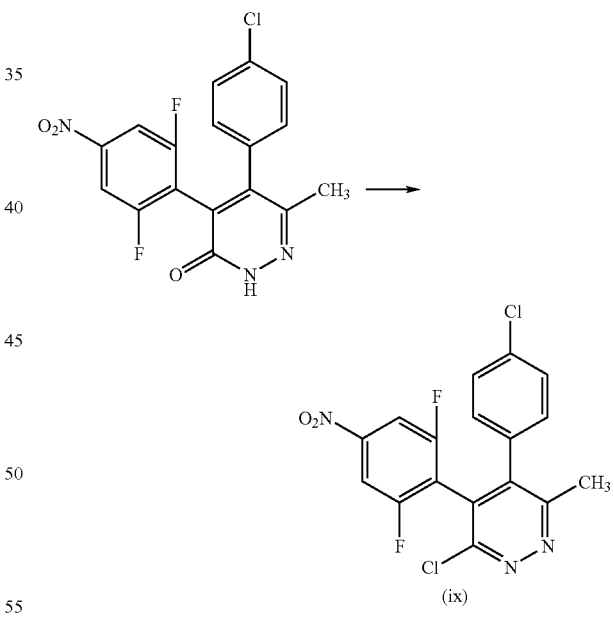

(ix)

6.0 g of 5-(4-chlorophenyl)-4-(2,6-difluoro-4-nitrophenyl)-6-methyl-2H-pyridazin-3-one and 30 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 6.15 g of 3-chloro-5-(4-chlorophenyl)-4-(2,6-difluoro-4-nitrophenyl)-6-methylpyridazine (hereinafter, referred to as compound (ix) of the present invention).

Compound (ix) of the present invention:
¹H-NMR (CDCl₃, TMS) δ (ppm): 2.57 (3H, s), 7.03 (2H, d, J=8.4 Hz), 7.33 (2H, d, J=8.4 Hz), 7.75-7.8 (2H, m)

PRODUCTION EXAMPLE 9

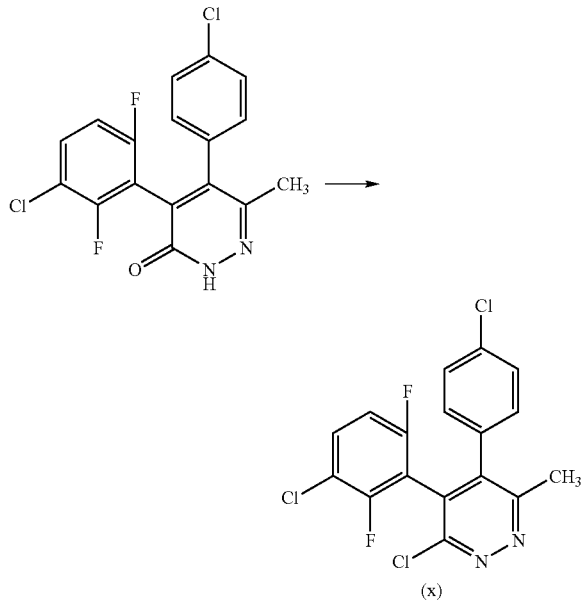

1.33 g of 4-(3-chloro-2,6-difluorophenyl)-5-(4-chlorophenyl)-6-methyl-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 1.33 g of 3-chloro-4-(3-chloro-2,6-difluorophenyl)-5-(4-chlorophenyl)-6-methylpyridazine (hereinafter, referred to as compound (x) of the present invention).

Compound (x) of the present invention:
¹H-NMR (CDCl₃, TMS) δ (ppm): 2.56 (3H, s), 6.8-6.85 (1H, m), 7.02 (2H, d, J=8.4 Hz), 7.32 (2H, d, J=8.4 Hz), 7.35-7.4 (1H, m)

PRODUCTION EXAMPLE 10

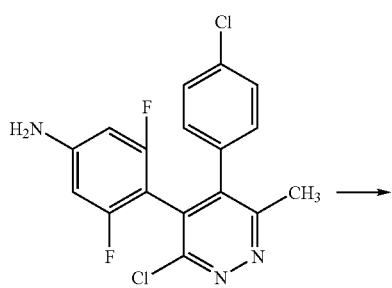

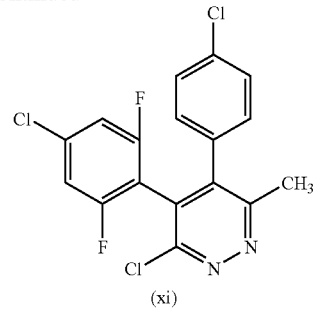

To a mixture of 323 mg of copper (II) chloride (CuCl₂), 309 mg of tert-butyl nitrite and 13 ml of acetonitrile was added 732 mg of 4-(4-amino-2,6-difluorophenyl)-3-chloro-5-(4-chlorophenyl)-6-methylpyridazine portion-wise under ice-cooling. Thereafter, the reaction mixture was stirred at room temperature for 2 hours. Then, the reaction mixture was poured into a mixture of ice and dilute hydrochloric acid, and extracted with ethyl acetate. The organic layer was washed sequentially with sodium bicarbonate water and saturated brine, and dried over anhydrous magnesium sulfate then concentrated. The residue was subjected to silica gel column chromatography (elution solvent; hexane:ethyl acetate=7:1), to obtain 0.62 g of 3-chloro-4-(4-chloro-2,6-difluorophenyl)-5-(4-chlorophenyl)-6-methylpyridazine (hereinafter, referred to as compound (xi) of the present invention).

Compound (xi) of the present invention
¹H-NMR (CDCl₃, TMS) δ (ppm): 2.54 (3H, s), 6.90 (2H, dd, J=4.8, 11.6 Hz), 7.02 (2H, d, J=8.4 Hz), 7.33 (2H, d, J=8.4 Hz)

PRODUCTION EXAMPLE 11

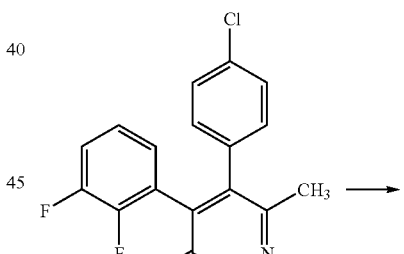

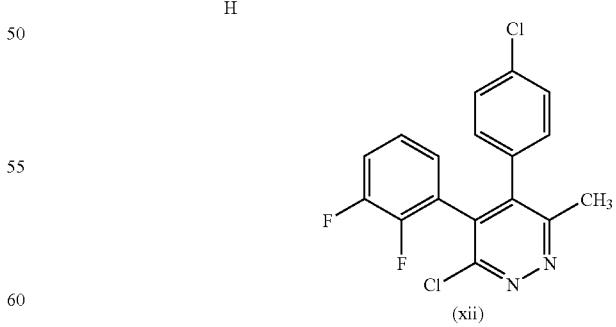

3.49 g of 5-(4-chlorophenyl)-4-(2,3-difluorophenyl)-6-methyl-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 3.66 g of 3-chloro-5-(4-chlorophenyl)-4-(2,3-difluorophenyl)-6-methyl pyridazine (hereinafter, referred to as compound (xii) of the present invention).

Compound (xii) of the present invention:
$^1$H-NMR (CDCl$_3$, TMS) δ (ppm): 2.54 (3H, s), 6.7-6.8 (1H, m), 6.95-7.1 (3H), 7.1-7.2 (1H, m), 7.29 (2H, d, J=8.4 Hz)

PRODUCTION EXAMPLE 12

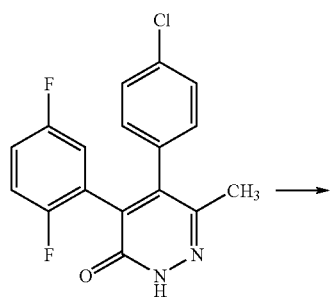

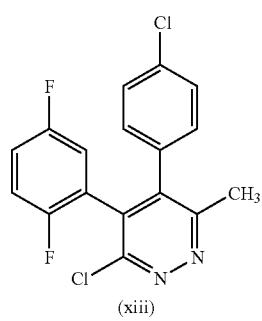

(xiii)

2.86 g of 5-(4-chlorophenyl)-4-(2,5-difluorophenyl)-6-methyl-2H-pyridazin-3-one and 6.5 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated. The residue was subjected to silica gel column chromatography (elution solvent; hexane:ethyl acetate=3:1, to obtain 2.89 g of 3-chloro-5-(4-chlorophenyl)-4-(2,5-difluorophenyl)-6-methyl pyridazine (hereinafter, referred to as compound (xiii) of the present invention).

Compound (xiii) of the present invention:
$^1$H-NMR (CDCl$_3$, TMS) δ (ppm): 2.54 (3H, s), 6.7-6.75 (1H, m), 6.95-7.05 (4H), 7.33 (2H, d, J=8.8 Hz)

PRODUCTION EXAMPLE 13

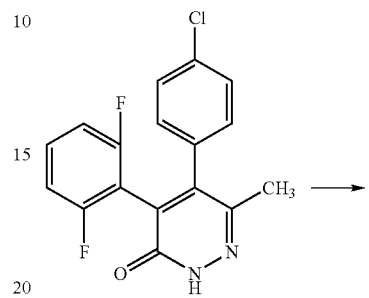

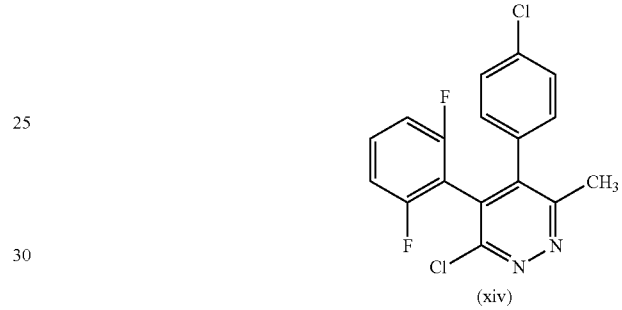

(xiv)

7.61 g of 5-(4-chlorophenyl)-4-(2,6-difluorophenyl)-6-methyl-2H-pyridazin-3-one and 40 ml of phosphorus oxychloride were mixed and stirred at 110° C. for 4 hours. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 8.52 g of 3-chloro-5-(4-chlorophenyl)-4-(2,6-difluorophenyl)-6-methyl pyridazine (hereinafter, referred to as compound (xiv) of the present invention).

Compound (xiv) of the present invention:
$^1$H-NMR (CDCl$_3$, TMS) δ (ppm): 2.54 (3H, s), 6.75-6.85 (2H, m), 6.9-7.0 (3H), 7.30 (2H, d, J=8.8 Hz)

PRODUCTION EXAMPLE 14

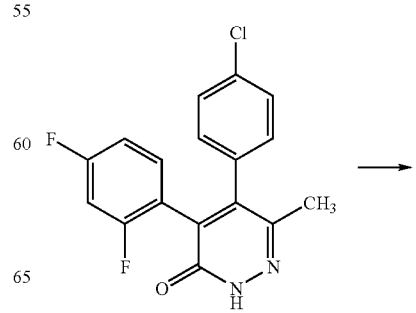

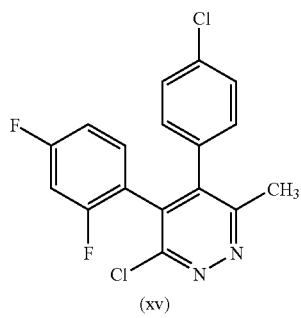

1.20 g of 5-(4-chlorophenyl)-4-(2,4-difluorophenyl)-6-methyl-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 1.22 g of 3-chloro-5-(4-chlorophenyl)-4-(2,4-difluorophenyl)-6-methyl pyridazine (hereinafter, referred to as compound (xv) of the present invention).

Compound (xv) of the present invention:
$^1$H-NMR (CDCl$_3$, TMS) δ (ppm): 2.53 (3H, s), 6.75-6.85 (2H), 6.9-7.0 (3H), 7.29 (2H, d, J=8.8 Hz)

PRODUCTION EXAMPLE 15

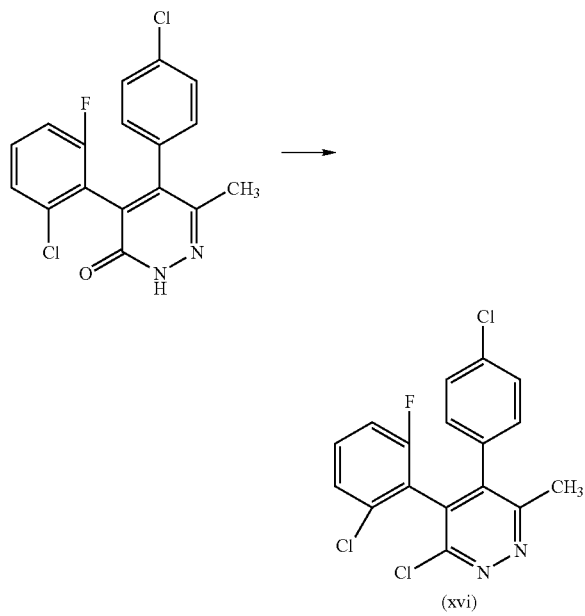

2.16 g of 4-(2-chloro-6-fluorophenyl)-5-(4-chlorophenyl)-6-methyl-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 2.21 g of 3-chloro-4-(2-chloro-6-fluorophenyl)-5-(4-chlorophenyl)-6-methylpyridazine (hereinafter, referred to as compound (xvi) of the present invention).

Compound (xvi) of the present invention:
$^1$H-NMR (CDCl$_3$, TMS) δ (ppm): 2.54 (3H, s), 6.9-7.0 (1H, m), 7.07 (2H, d, J=8.8 Hz), 7.17 (1H, d, J=8.0 Hz), 7.2-7.3 (3H)

PRODUCTION EXAMPLE 16

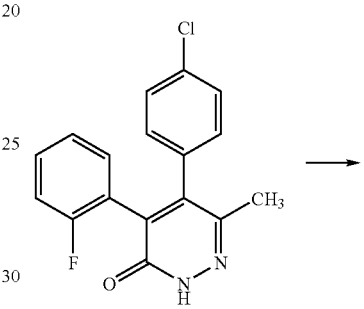

1.95 g of 5-(4-chlorophenyl)-4-(2-fluorophenyl)-6-methyl-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 1.96 g of 3-chloro-5-(4-chlorophenyl)-4-(2-fluorophenyl)-6-methylpyridazine (hereinafter, referred to as compound (xvii) of the present invention).

Compound (xvii) of the present invention:
$^1$H-NMR (CDCl$_3$, TMS) δ (ppm): 2.53 (3H, s), 6.95-7.1 (5H), 7.25-7.35 (3H)

PRODUCTION EXAMPLE 17

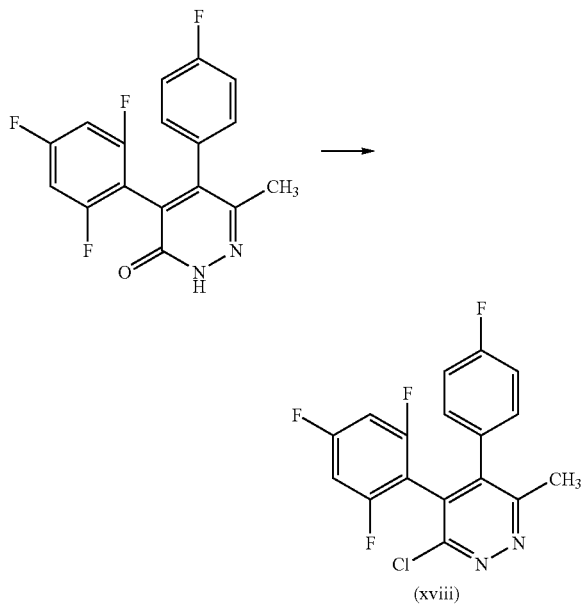

2.36 g of 5-(4-fluorophenyl)-6-methyl-4-(2,4,6-trifluorophenyl)-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 2.34 g of 3-chloro-5-(4-fluorophenyl)-6-methyl-4-(2,4,6-trifluorophenyl)pyridazine (hereinafter, referred to as compound (xviii) of the present invention).

Compound (xviii) of the present invention:
$^1$H-NMR (CDCl$_3$, TMS) δ (ppm): 2.54 (3H, s), 6.6-6.65 (2H, m), 7.0-7.1 (4H, m)

PRODUCTION EXAMPLE 18

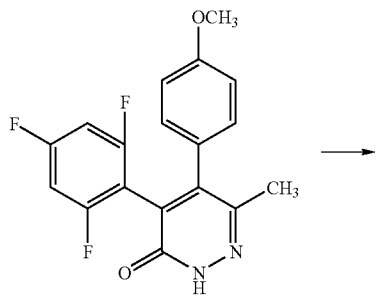

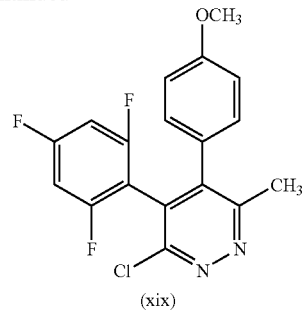

2.06 g of 5-(4-methoxyphenyl)-6-methyl-4-(2,4,6-trifluorophenyl)-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 2.14 g of 3-chloro-5-(4-methoxyphenyl)-6-methyl-4-(2,4,6-trifluorophenyl)pyridazine (hereinafter, referred to as compound (xix) of the present invention).

Compound (xix) of the present invention:
$^1$H-NMR (CDCl$_3$, TMS) δ (ppm): 2.55 (3H, s), 3.80 (3H, s), 6.55-6.65 (2H, m), 6.83 (2H, d, J=8.4 Hz), 6.98 (2H, d, J=8.4 Hz)

PRODUCTION EXAMPLE 19

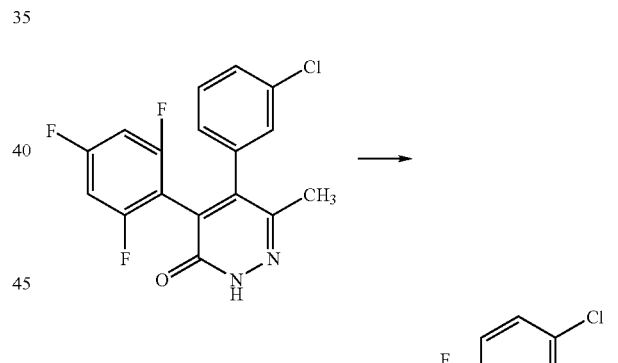

2.34 g of 5-(3-chlorophenyl)-6-methyl-4-(2,4,6-trifluorophenyl)-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 2.39 g of 3-chloro-5-(3-chlorophenyl)-6-methyl-4-(2,4,6-trifluorophenyl)pyridazine (hereinafter, referred to as compound (xx) of the present invention).

Compound (xx) of the present invention:
¹H-NMR (CDCl₃, TMS) δ (ppm): 2.55 (3H, s), 6.6-6.7 (2H, br), 6.96 (1H, d, J=7.8 Hz), 7.09 (1H), 7.3-7.35 (2H)

PRODUCTION EXAMPLE 20

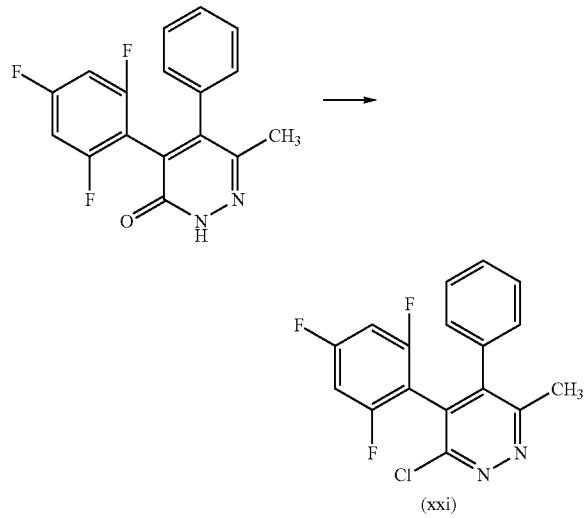

1.67 g of 6-methyl-5-phenyl-4-(2,4,6-trifluorophenyl)-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 1.74 g of 3-chloro-6-methyl-5-phenyl-4-(2,4,6-trifluorophenyl)pyridazine (hereinafter, referred to as compound (xxi) of the present invention).

Compound (xxi) of the present invention:
¹H-NMR (CDCl₃, TMS) δ (ppm): 2.54 (3H, s), 6.55-6.65 (2H, m), 7.05-7.1 (2H), 7.3-7.35 (3H)

PRODUCTION EXAMPLE 21

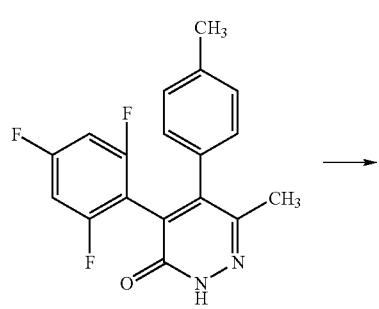

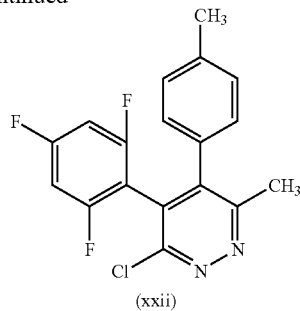

19.77 g of 6-methyl-5-(4-methylphenyl)-4-(2,4,6-trifluorophenyl)-2H-pyridazin-3-one and 100 ml of phosphorus oxychloride were mixed and stirred at 110° C. for 1 hour. The reaction mixture was allowed to cool down to room temperature and concentrated under reduced pressure. To the residue was added chloroform and ice water, and was separated to two layer. The organic layer was washed sequentially with water and saturated brine, and dried over anhydrous sodium sulfate, then, concentrated under reduced pressure, to obtain 19.90 g of 3-chloro-6-methyl-5-(4-methylphenyl)-4-(2,4,6-trifluorophenyl)pyridazine (hereinafter, referred to as compound (xxii) of the present invention).

Compound (xxii) of the present invention:
¹H-NMR (CDCl₃, TMS) δ (ppm): 2.32 (3H, s), 2.55 (3H, s), 6.55-6.65 (2H, m), 6.94 (2H, d, J=8.4 Hz), 7.12 (2H, d, J=8.4 Hz)

PRODUCTION EXAMPLE 22

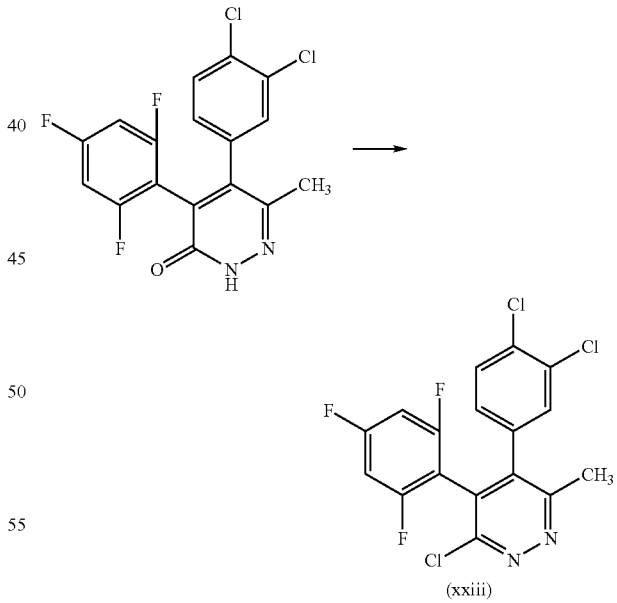

1.75 g of 5-(3,4-dichlorophenyl)-6-methyl-4-(2,4,6-trifluorophenyl)-2H-pyridazin-3-one and 6 ml of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 1.80 g of 3-chloro-5-(3,4-dichlorophenyl)-6-methyl-4-(2,4,6-trifluoro phenyl)pyridazine (hereinafter, referred to as compound (xxiii) of the present invention).

Compound (xxiii) of the present invention:
$^1$H-NMR (CDCl$_3$, TMS) δ (ppm): 2.55 (3H, s), 6.67 (2H, br t), 6.93 (1H, dd), 7.20 (1H, d), 7.43 (1H, d)

PRODUCTION EXAMPLE 23

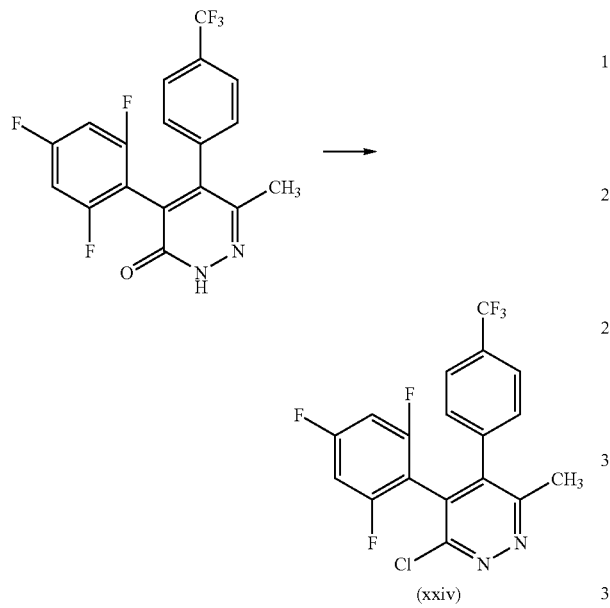

2.43 g of 6-methyl-5-(4-trifluoromethylphenyl)-4-(2,4,6-trifluorophenyl)-2H-pyridazin-3-one and 10 g of phosphorus oxychloride were mixed and stirred at 110° C. for 1 hour. The reaction mixture was allowed to cool down to room temperature and concentrated under reduced pressure. To the residue was added ethyl acetate and ice water, and was separated to two layer. The organic layer was washed sequentially with water and saturated brine, and dried over anhydrous sodium sulfate, then, concentrated under reduced pressure, to obtain 2.50 g of 3-chloro-6-methyl-5-(4-trifluoromethylphenyl)-4-(2,4,6-trifluorophenyl)pyridazine (hereinafter, referred to as compound (xxiv) of the present invention).

Compound (xxiv) of the present invention:
$^1$H-NMR (CDCl$_3$, TMS) δ (ppm): 2.53 (3H, s), 6.6-6.7 (2H, m), 7.23 (2H, d, J=8.0 Hz), 7.62 (2H, d, J=8.0 Hz)

Next, reference production examples for production of intermediates of the compounds of the present invention are shown.

REFERENCE PRODUCTION EXAMPLE 1

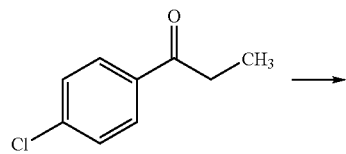

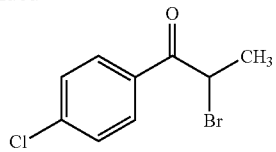

To a mixture of 10.12 g of 4'-chloropropiophenone, 0.1 ml of hydrobromic acid (48% aqueous solution) and 60 ml of acetic acid was added 3.1 ml of bromine at 0° C. under a nitrogen atmosphere, and stirred at room temperature for 1 hour. Thereafter, the reaction mixture was concentrated under reduced pressure, to obtain 14.34 g of 2-bromo-4'-chloropropiophenone.

$^1$H-NMR (CDCl$_3$, TMS) δ (ppm): 1.90 (3H, d, J=6.5 Hz), 5.22 (1H, q, J=6.5 Hz), 7.46 (2H, d, J=8.7 Hz), 7.97 (2H, d, J=8.7 Hz)

REFERENCE PRODUCTION EXAMPLE 2

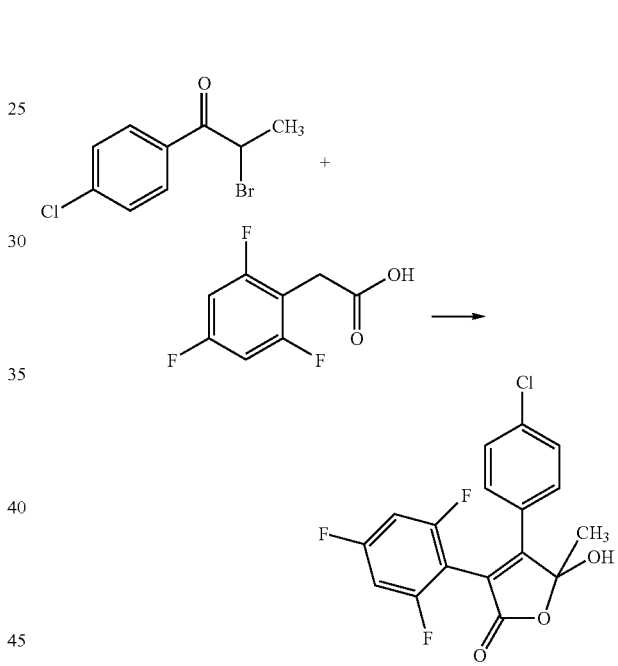

14.32 g of 2-bromo-4'-chloropropiophenone, 12.08 g of 2,4,6-trifluorophenylacetic acid, 170 ml of acetonitrile and 6.43 g of triethylamine were mixed and stirred at room temperature for overnight. To this mixture was added 210 ml of acetonitrile at room temperature, then, the mixture was cooled to 0° C., and 21.5 g of DBU was added over 25 minutes. The mixture was stirred for 2 hours at 0° C. Thereafter, air was blown into the resultant mixture at room temperature while stirring for 4.5 hours. To the reaction mixture was added 1 mol/L hydrochloric acid, and extracted with ethyl acetate. The organic layer was washed sequentially with saturated sodium bicarbonate aqueous solution and saturated brine, and dried over anhydrous magnesium sulfate, then, concentrated under reduced pressure. The resulting residue was subjected to silica gel chromatography to obtain 17.89 g of 4-(4-chlorophenyl)-5-hydroxy-5-methyl-3-(2,4,6-trifluorophenyl)-2 (5H)-furanone.

$^1$H-NMR (CDCl$_3$, TMS) δ (ppm): 1.76 (3H, s), 4.20 (1H, br), 6.63 (1H, br), 6.80 (1H, br), 7.33 (2H, d, J=8.7 Hz), 7.48 (2H, d, J=8.7 Hz)

Next, compounds produced in a similar manner as this production example and their NMR data are shown.

4-(4-chlorophenyl)-5-hydroxy-5-methyl-3-(2,3,6-trifluorophenyl)-2 (5H)-furanone;
 $^1$H-NMR (DMSO-d6, TMS) δ (ppm): 1.66 (3H, s), 7.15-7.4 (1H, br), 7.51 (4H, s), 7.6-7.7 (1H, m), 8.39 (1H, s)

4-(4-chlorophenyl)-5-hydroxy-5-methyl-3-(2,4,5-trifluorophenyl)-2 (5H)-furanone;
 $^1$H-NMR (DMSO-d6, TMS) δ (ppm): 1.61 (3H, s), 7.4-7.65 (6H), 8.23 (1H, br)

4-(4-chlorophenyl)-5-hydroxy-5-methyl-3-(2,3,5-trifluorophenyl)-2 (5H)-furanone;
 $^1$H-NMR (DMSO-d6, TMS) δ (ppm): 1.62 (3H, s), 7.1-7.2 (1H, br), 7.45-7.55 (4H), 7.6-7.7 (1H, br), 8.22 (1H, s)

4-(4-chlorophenyl)-3-(2,6-difluoro-4-nitrophenyl)-5-hydroxy-5-methyl-2(5H)-furanone;
 $^1$H-NMR (DMSO-d6, TMS) δ (ppm): 1.67 (3H, s), 7.45-7.55 (4H), 8.05-8.3 (2H, br), 8.47 (1H, s)

3-(3-chloro-2,6-difluorophenyl)-4-(4-chlorophenyl)-5-hydroxy-5-methyl-2(5H)-furanone;
 $^1$H-NMR (DMSO-d6, TMS) δ (ppm): 1.65 (3H, s), 7.28 (1H, br), 7.50 (4H, s), 7.78 (1H, br dd, J=8.8, 10.4 Hz), 8.40 (1H, br s)

4-(4-chlorophenyl)-3-(2,3-difluorophenyl)-5-hydroxy-5-methyl-2(5H)-furanone;
 $^1$H-NMR (DMSO-d6, TMS) δ (ppm): 1.63 (3H, s), 7.15-7.25 (1H, m), 7.25-7.35 (1H, m), 7.4-7.6 (5H), 8.18 (1H, s)

4-(4-chlorophenyl)-3-(2,5-difluorophenyl)-5-hydroxy-5-methyl-2(5H)-furanone;
 $^1$H-NMR (DMSO-d6, TMS) δ (ppm): 1.60 (3H, s), 7.15-7.55 (7H), 8.15 (1H, s)

4-(4-chlorophenyl)-3-(2,6-difluorophenyl)-5-hydroxy-5-methyl-2(5H)-furanone;
 $^1$H-NMR (CDCl$_3$, TMS) δ (ppm): 1.73 (3H, s), 4.2-4.4 (1H, br), 6.75-6.85 (1H, m), 6.9-7.0 (1H, m), 7.31 (2H, d, J=8.8 Hz), 7.3-7.4 (1H, m), 7.45 (2H, d, J=8.8 Hz)

4-(4-chlorophenyl)-3-(2,4-difluorophenyl)-5-hydroxy-5-methyl-2(5H)-furanone;
 $^1$H-NMR (CDCl$_3$, TMS) δ (ppm): 1.74 (3H, s), 3.83 (1H, s), 6.75-6.85 (1H, m), 6.9-7.0 (1H, m), 7.32 (2H, d, J=8.8 Hz), 7.35-7.45 (1H, m), 7.46 (2H, d, J=8.8 Hz)

4-(4-chlorophenyl)-3-(2-fluorophenyl)-5-hydroxy-5-methyl-2(5H)-furanone;
 $^1$H-NMR (CDCl$_3$, TMS) δ (ppm): 1.73 (3H, s), 4.37 (1H, s), 7.04 (1H, t, J=8.8 Hz), 7.17 (1H, t, J=7.8 Hz), 7.28 (2H, d, J=8.4 Hz), 7.3-7.4 (2H), 7.46 (2H, d, J=8.4 Hz)

4-(4-fluorophenyl)-5-hydroxy-5-methyl-3-(2,4,6-trifluorophenyl)-2(5H)-furanone;
 $^1$H-NMR (CDCl$_3$, TMS) δ (ppm): 1.77 (3H, s), 4.42 (1H, br s), 6.55-6.95 (2H), 7.0-7.1 (2H, m), 7.5-7.6 (2H, m)

5-hydroxy-4-(4-methoxyphenyl)-5-methyl-3-(2,4,6-trifluorophenyl)-2(5H)-furanone;
 $^1$H-NMR (CDCl$_3$, TMS) δ (ppm): 1.80 (3H, s), 3.82 (3H, s), 4.16 (1H, br), 6.6-6.7 (1H, br), 6.75-6.85 (1H, m), 6.76 (2H, d, J=8.8 Hz), 7.54 (2H, d, J=8.8 Hz)

4-(3-chlorophenyl)-5-hydroxy-5-methyl-3-(2,4,6-trifluorophenyl)-2(5H)-furanone;
 $^1$H-NMR (CDCl$_3$, TMS) δ (ppm): 1.77 (3H, s), 4.27 (1H, br s), 6.65-6.8 (2H), 7.25-7.4 (3H), 7.57 (1H)

5-hydroxy-5-methyl-4-phenyl-3-(2,4,6-trifluorophenyl)-2(5H)-furanone;
 $^1$H-NMR (CDCl$_3$, TMS) δ (ppm): 1.79 (3H, s), 4.17 (1H, br), 6.65-6.8 (2H), 7.3-7.5 (3H), 7.5-7.6 (2H)

5-hydroxy-5-methyl-4-(4-methylphenyl)-3-(2,4,6-trifluorophenyl)-2(5H)-furanone;
 $^1$H-NMR (CDCl$_3$, TMS) δ (ppm): 1.80 (3H, s), 2.30 (3H, s), 3.93 (1H, br), 6.6-6.7 (1H, br), 6.75-6.9 (1H, br), 7.16 (2H, d, J=8 Hz), 7.44 (2H, d, J=8 Hz)

4-(3,4-dichlorophenyl)-5-hydroxy-5-methyl-3-(2,4,6-trifluorophenyl)-2(5H)-furanone;
 $^1$H-NMR (CDCl$_3$, TMS) δ (ppm): 1.76 (3H, s), 4.4-4.8 (1H, br), 6.65 (1H, br), 6.8 (1H, br), 7.31 (1H, dd, J=2, 8.4 Hz), 7.42 (1H, d, J=8.4 Hz), 7.70 (1H, d, J=2 Hz)

5-hydroxy-5-methyl-4-(4-trifluoromethylphenyl)-3-(2,4,6-trifluorophenyl)-2(5H)-furanone;
 $^1$H-NMR (CDCl$_3$, TMS) δ (ppm): 1.78 (3H, s), 4.05 (1H, br s), 6.55-6.9 (2H), 6.6-6.7 (4H)

REFERENCE PRODUCTION EXAMPLE 3

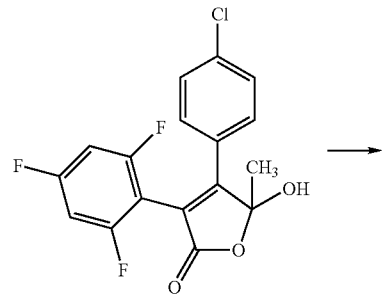

17.03 g of 4-(4-chlorophenyl)-5-hydroxy-5-methyl-3-(2,4,6-trifluorophenyl)-2(5H)-furanone, 2.64 g of hydrazine monohydrate and 240 ml of 1-butanol were mixed, and stirred at 90° C. for 3 hours. Then, the reaction mixture was cooled to 0° C. The resulting solid was collected by filtration. The collected solid was washed using hexane and t-butyl methyl ether, and dried under reduced pressure to obtain 6.99 g of 5-(4-chlorophenyl)-6-methyl-4-(2,4,6-trifluorophenyl)-2H-pyridazin-3-one.
 $^1$H-NMR (CDCl$_3$, TMS) δ (ppm): 2.11 (3H, s), 6.57 (2H, dd, J=7.3, 8.7 Hz), 7.03 (2H, d, J=8.3 Hz), 7.30 (2H, d, J=8.3 Hz), 11.04 (1H, s)

Next, compounds produced in a similar manner as this production example and their NMR data are shown.

5-(4-chlorophenyl)-6-methyl-4-(2,3,6-trifluorophenyl)-2H-pyridazin-3-one
 $^1$H-NMR (DMSO-d6, TMS) δ (ppm): 2.06 (3H, s), 7.05 (1H, br), 7.19 (2H, br), 7.35-7.45 (3H)

5-(4-chlorophenyl)-6-methyl-4-(2,4,5-trifluorophenyl)-2H-pyridazin-3-one
 $^1$H-NMR (DMSO-d6, TMS) δ (ppm): 2.02 (3H, s), 7.10-7.45 (6H), 13.23 (1H, s)

5-(4-chlorophenyl)-6-methyl-4-(2,3,5-trifluorophenyl)-2H-pyridazin-3-one
 $^1$H-NMR (DMSO-d6, TMS) δ (ppm): 2.03 (3H, s), 6.93 (1H, br), 7.17 (1H, br), 7.33 (1H, br), 7.35-7.5 (3H), 13.28 (1H, s)

5-(4-chlorophenyl)-4-(2,6-difluoro-4-nitrophenyl)-6-methyl-2H-pyridazin-3-one

¹H-NMR (DMSO-d6, TMS) δ (ppm): 2.07 (3H, s), 7.20 (2H, d, J=8 Hz), 7.40 (2H, d, J=8 Hz), 7.95-8.05 (2H, m)

4-(3-chloro-2,6-difluorophenyl)-5-(4-chlorophenyl)-6-methyl-2H-pyridazin-3-one

¹H-NMR (CDCl₃, TMS) δ (ppm): 2.12 (3H, s), 6.75-6.8 (1H, m), 7.04 (2H, d, J=8.8 Hz), 7.25-7.35 (3H), 11.86 (1H, br s)

5-(4-chlorophenyl)-4-(2,3-difluorophenyl)-6-methyl-2H-pyridazin-3-one

¹H-NMR (DMSO-d6, TMS) δ (ppm): 2.02 (3H, s), 6.85-6.95 (1H m), 7.0-7.15 (2H), 7.25-7.45 (4H), 13.22 (1H, s)

5-(4-chlorophenyl)-4-(2,5-difluorophenyl)-6-methyl-2H-pyridazin-3-one

¹H-NMR (DMSO-d6, TMS) δ (ppm): 2.01 (3H, s), 7.0-7.4 (7H), 13.19 (1H, s)

5-(4-chlorophenyl)-4-(2,6-difluorophenyl)-6-methyl-2H-pyridazin-3-one

¹H-NMR (CDCl₃, TMS) δ (ppm): 2.11 (3H, s), 6.65-6.8 (2H), 6.9-7.01 (3H), 7.25-7.35 (2H), 11.24 (1H, br)

5-(4-chlorophenyl)-4-(2,4-difluorophenyl)-6-methyl-2H-pyridazin-3-one

¹H-NMR (CDCl₃, TMS) δ (ppm): 2.11 (3H, s), 6.65-6.8 (2H), 6.95 (1H, br), 6.95-7.1 (2H), 7.2-7.35 (2H), 11.82 (1H, br s)

4-(2-chloro-6-fluorophenyl)-5-(4-chlorophenyl)-6-methyl-2H-pyridazin-3-one

¹H-NMR (CDCl₃ (containing one drop of DMSO-D6), TMS) δ (ppm): 2.11 and 2.12 (total 3H, each s), 6.85-6.9 (1H, m), 7.05-7.35 (6H), 12.37 (1H, br s)

5-(4-chlorophenyl)-4-(2-fluorophenyl)-6-methyl-2H-pyridazin-3-one

¹H-NMR (CDCl₃ (containing one drop of DMSO-D6), TMS) δ (ppm): 2.11 (3H, s), 6.9-7.1 (5H), 7.2-7.3 (3H), 12.09 (1H, br s)

5-(4-fluorophenyl)-6-methyl-4-(2,4,6-trifluorophenyl)-2H-pyridazin-3-one

¹H-NMR (CDCl₃, TMS) δ (ppm): 2.12 (3H, s), 6.5-6.6 (2H, m), 6.95-7.1 (4H), 11.57 (1H, br s)

5-(4-methoxyphenyl)-6-methyl-4-(2,4,6-trifluorophenyl)-2H-pyridazin-3-one

¹H-NMR (CDCl₃, TMS) δ (ppm): 2.14 (3H, s), 3.79 (3H, s), 6.5-6.6 (2H, m), 6.82 (2H, d, J=8.8 Hz), 7.00 (2H, d, J=8.8 Hz), 10.85 (1H, br s)

5-(3-chlorophenyl)-6-methyl-4-(2,4,6-trifluorophenyl)-2H-pyridazin-3-one

¹H-NMR (CDCl₃, TMS) δ (ppm): 2.13 (3H, s), 6.5-6.65 (2H, br), 6.98 (2H, d, J=7.2 Hz), 7.11 (1H, s), 7.25-7.35 (2H), 11.97 (1H, br s)

6-methyl-5-phenyl-4-(2,4,6-trifluorophenyl)-2H-pyridazin-3-one

¹H-NMR (CDCl₃, TMS) δ (ppm): 2.12 (3H, s), 6.45-6.55 (2H, m), 7.05-7.1 (2H), 7.25-7.35 (3H), 11.93 (1H, br s)

6-methyl-5-(4-methylphenyl)-4-(2,4,6-trifluorophenyl)-2H-pyridazin-3-one

¹H-NMR (CDCl₃, TMS) δ (ppm): 2.12 (3H, s), 2.31 (3H, s), 6.5-6.6 (2H, m), 6.96 (2H, d, J=8 Hz), 7.10 (2H, d, J=8 Hz), 10.68 (1H, br s)

5-(3,4-dichlorophenyl)-6-methyl-4-(2,4,6-trifluorophenyl)-2H-pyridazin-3-one

¹H-NMR (CDCl₃, TMS) δ (ppm): 2.13 (3H, s), 6.61 (1H, br t), 6.94 (1H, dd, J=2, 8.4 Hz), 7.22 (1H, d, J=2 Hz), 7.41 (1H, d, J=8.4 Hz), 10.76 (1H, br s)

6-methyl-5-(4-trifluoromethylphenyl)-4-(2,4,6-trifluorophenyl)-2H-pyridazin-3-one ¹H-NMR (CDCl₃, TMS) δ (ppm): 2.10 (3H, s), 6.57 (2H, dd, J=7.2, 8.8 Hz), 7.25 (2H, d, J=8.0 Hz), 7.60 (2H, d, J=8.0 Hz), 11.13 (1H, br s)

REFERENCE PRODUCTION EXAMPLE 4

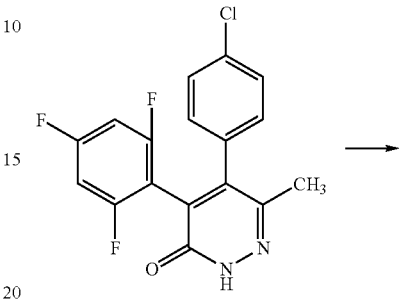

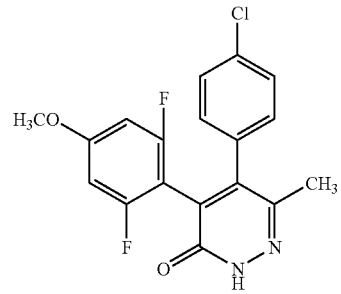

0.35 g of 5-(4-chlorophenyl)-6-methyl-4-(2,4,6-trifluorophenyl)-2H-pyridazin-3-one, 0.96 g of sodium methoxide (28%-methanol solution) and 6 ml of methanol were mixed and stirred for 14 hours under reflux with heating. Next, to the reaction mixture was added 0.96 g of sodium methoxide (28% methanol solution), and stirred for 9 hours under reflux with heating. The reaction mixture was cooled to room temperature. Water was added to the reaction mixture, and extracted with ethyl acetate. The organic layer was washed with water, and dried over anhydrous magnesium sulfate, then, concentrated under reduced pressure. The residue was subjected to silica gel column chromatography (elution solvent: hexane+tert-butyl methyl ether), to obtain 0.25 g of 5-(4-chlorophenyl)-4-(2,6-difluoro-4-methoxyphenyl)-6-methyl-2H-pyridazin-3-one.

¹H-NMR (CDCl₃, TMS) δ (ppm): 2.11 (3H, s), 3.73 (3H, s), 6.34 (2H, dd, J=4, 12 Hz), 7.04 (2H, d, J=12 Hz), 7.29 (2H, d, J=12 Hz), 11.57 (1H, br s)

Next, compounds produced in a similar manner as this production example and their NMR data are shown.

5-(4-chlorophenyl)-4-(2,6-difluoro-4-ethoxyphenyl)-6-methyl-2H-pyridazin-3-one

¹H-NMR (CDCl₃, TMS) δ (ppm): 1.37 (3H, t, J=7.2 Hz), 2.10 (3H, s), 3.93 (2H, q, J=7.2 Hz), 6.32 (2H, dd, J=5.2, 14.4 Hz), 7.04 (2H, d, J=8.8 Hz), 7.28 (2H, d, J=8.8 Hz), 11.46 (1H, br s)

REFERENCE PRODUCTION EXAMPLE 5

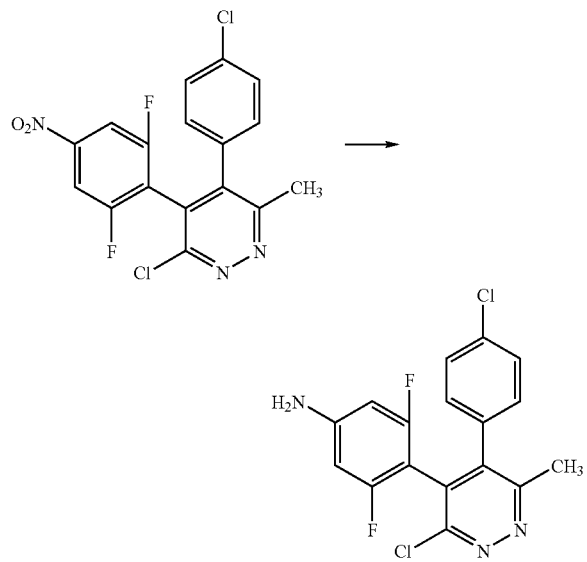

(ix)

A mixture of 3.91 g of iron (powder), 60 ml of acetic acid and 60 ml of water was stirred for 0.5 hours at 70 to 80° C. Onto this mixture was dropped an ethyl acetate (120 ml) solution of 5.44 g of the compound (ix) of the present invention at 70 to 80° C. over 40 minutes. Thereafter, the reaction mixture was filtrated through celite. The filtrate was separated to two layer. The organic layer was washed sequentially with saturated brine, saturated sodium bicarbonate water (3 times) and saturated brine, and dried over anhydrous magnesium sulfate, then, concentrated under reduced pressured to obtain 4.98 g of 4-(4-amino-2,6-difluorophenyl)-3-chloro-5-(4-chlorophenyl)-6-methylpyridazine.

$^1$H-NMR (CDCl$_3$, TMS) δ (ppm): 2.51 (3H, s), 4.00 (2H, br s), 6.05-6.15 (2H, m), 7.02 (2H, d, J=8.4 Hz), 7.31 (2H, d, J=8.4 Hz)

Next, Formulation examples are shown. Part means part by weight.

FORMULATION EXAMPLE 1

Fifty parts of each of compounds (i) to (xxiv) of the present invention, 3 parts of calcium ligninsulfonate, 2 parts of magnesium laurylsulfate and 45 parts of synthetic hydrated silica are pulverized and mixed well to give wettable powders of each compound.

FORMULATION EXAMPLE 2

Twenty parts of each of compounds (i) to (xxiv) of the present invention and 1.5 parts of sorbitan trioleate are mixed with 28.5 parts of an aqueous solution containing 2 parts of polyvinyl alcohol, and wet-pulverized finely. To the obtained mixture, 40 parts of an aqueous solution containing 0.05 part of xanthan gum and 0.1 part of aluminum magnesium silicate is added and further 10 parts of propylene glycol are added to give a flowable of each compound.

FORMULATION EXAMPLE 3

Two parts of each of compounds (i) to (xxiv) of the present invention, 88 parts of kaolin clay and 10 parts of talc are pulverized and mixed well to give a dust of each compound.

FORMULATION EXAMPLE 4

Five parts of each of compounds (i) to (xxiv) of the present invention, 14 parts of polyoxyethylenestyryl phenyl ether, 6 parts of calcium dodecylbenzenesulfonate and 75 parts of xylene are mixed well to give an emulsifiable concentrate of each compound.

FORMULATION EXAMPLE 5

Two parts of each of compounds (i) to (xxiv) of the present invention, 1 part of synthetic hydrated silica, 2 parts of calcium ligninsulfonate, 30 parts of bentonite and 65 parts of kaolin clay are pulverized and mixed well, and water is added thereto and kneaded, granulated and dried to give a granule of each compound.

FORMULATION EXAMPLE 6

Ten parts of each of the compounds (i) to (xxiv) of present invention, 35 parts of white carbon containing 50% by weight of ammonium polyoxyethylenealkyl ether sulfate and 55 parts of water are mixed and wet pulverized finely to give a formulation of each compound.

Next, a fact that the compound of the present invention is effective for controlling plant diseases is shown by test examples.

TEST EXAMPLE 1

A plastic pot was filled with sandy loam, cucumber (cultivar: Sagami Hanjiro) was sowed, and grown in a greenhouse for 10 days. Each of the compounds (i) to (xxiv) of the present invention was formulated according to Formulation Example 6, then, diluted with water to a concentration of 500 ppm. Each of the resulting diluted solutions was sprayed on stems and leaves so as to sufficiently adhere to the surface of cucumber cotyledones. After spraying, the plant was air-dried, and a PDA medium containing spores of *Botrytis cinerea* was placed on the surface of cucumber cotyledones. Then, the cucumber was left under humid condition at 12° C. for 5 days. Thereafter, the lesion area of the plant was visually observed. As a result, the lesion area of the cucumber treated with the compounds (i) to (xxiv) of the present invention was 10% or less of the lesion area of non-treated cucumber.

TEST EXAMPLE 2

A plastic pot was filled with sandy loam, paddy (cultivar: NihonBare) was sowed, and grown in a greenhouse for 15 days. Each of the compounds (i) to (xxiv) of the present invention was formulated according to Formulation Example 6, then, diluted with water to a concentration of 500 ppm. Each of the resulting diluted solutions was sprayed on stem and leaves so as to sufficiently adhere to the surface of the paddy leaves. After spraying, the plant was air-dried. Plastic pots containing planted paddy affected by *Pyricularia oryzae* were placed around the plastic pot of paddy, and this condition was left under humid condition at 22° C. for 6 days. Thereafter, a controlling effect was checked. As a result, the lesion area of the paddy treated with the compounds (i) to (xxiv) of the present invention was 10% or less of the lesion area of non-treated paddy.

TEST EXAMPLE 3

A plastic pot was filled with sandy loam, Japanese radish (cultivar: Wase 40 nichi) was sowed, and grown in a greenhouse for 5 days. Each of the compounds (i) to (xxiv) of the present invention was formulated according to Formulation Example 6, then, diluted with water to a concentration of 500 ppm. Each of the resulting diluted solutions was sprayed on stem and leaves so as to sufficiently adhere to the radish. After spraying, the plant was air-dried, and inoculated with spores of *Alternaria brassicicola*. Then, this radish was left under humid condition at 23° C. overnight, further, left in a greenhouse for 3 days. Thereafter, a controlling effect was checked. As a result, the lesion area of the radish treated with the compounds (i) to (xxiv) of the present invention was 10% or less of the lesion area of non-treated radish.

INDUSTRIAL APPLICABILITY

The plant diseases can be controlled by using the compound of the present invention.

The invention claimed is:

1. A compound represented by formula (3):

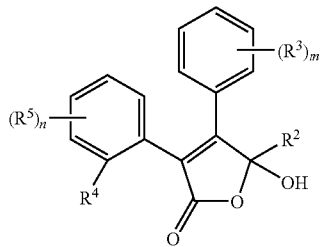

(3)

wherein, $R^2$ represents a C1-C4 alkyl group;

$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;

m represents an integer of 0 to 5; provided that, when m represents an integer of 2 or more, each of $R^3$s is same or different;

$R^4$ represents a halogen atom, a nitro group, a cyano group, a C1-C4 alkyl group optionally substituted by at least one halogen atom or a C1-C4 alkoxy group optionally substituted by at least one halogen atom;

$R^5$ represents a halogen atom, a nitro group, a cyano group, a C1-C4 alkyl group optionally substituted by at least one halogen atom or a C1-C4 alkoxy group optionally substituted by at least one halogen atom;

n represents an integer of 0 to 4; provided that, when n represents an integer of 2 or more, each of $R^5$s is same or different.

* * * * *